US011650625B1

(12) United States Patent
Grajewski et al.

(10) Patent No.: US 11,650,625 B1
(45) Date of Patent: May 16, 2023

(54) MULTI-SENSOR WEARABLE DEVICE WITH AUDIO PROCESSING

(71) Applicant: AMAZON TECHNOLOGIES, INC., Seattle, WA (US)

(72) Inventors: Christopher Raymond Grajewski, Sammamish, WA (US); Maya Shirish Sathaye, Seattle, WA (US); Joshua Watson, Seattle, WA (US); Matthew Wilkinson, Kirkland, WA (US); Sameet Ramakrishnan, Saratoga, CA (US)

(73) Assignee: AMAZON TECHNOLOGIES, INC., Seattle, WA (US)

( * ) Notice: Subject to any disclaimer, the term of this patent is extended or adjusted under 35 U.S.C. 154(b) by 873 days.

(21) Appl. No.: 16/456,418

(22) Filed: Jun. 28, 2019

(51) Int. Cl.

| | |
|---|---|
| ***G10L 25/78*** | (2013.01) |
| ***A61B 5/24*** | (2021.01) |
| ***G06F 1/16*** | (2006.01) |
| ***A61B 5/00*** | (2006.01) |
| ***A61B 5/11*** | (2006.01) |

(Continued)

(52) U.S. Cl.
CPC ............ *G06F 1/163* (2013.01); *A61B 5/1118* (2013.01); *A61B 5/24* (2021.01); *A61B 5/681* (2013.01); *A61B 5/742* (2013.01); *G06F 13/4282* (2013.01); *G10L 25/78* (2013.01); *G10L 25/93* (2013.01); *A61B 2562/0219* (2013.01); *G10L 2025/783* (2013.01)

(58) Field of Classification Search
CPC ......... G10L 15/22; G10L 15/28; G10L 25/78; G10L 2025/783; A61B 5/24
USPC ......... 704/210, 215, 233, 275; 600/301, 485
See application file for complete search history.

(56) References Cited

U.S. PATENT DOCUMENTS

2003/0142813 A1* 7/2003 Domer .................. H04M 9/082
2006/0018457 A1* 1/2006 Unno .................... H04M 9/082

(Continued)

FOREIGN PATENT DOCUMENTS

EP 1286328 * 2/2003 ............. G10L 11/02

OTHER PUBLICATIONS

Grimm, et al., "Primitives-based evaluation and estimation of emotions in speech", ScienceDirect, Speech Communication 49 (2007), Dec. 21, 2006, pp. 787-800. Retrieved from the Internet: URL: chrome-extension://efaidnbmnnnibpcajpcglclefindmkaj/https://sail.usc.edu/publications/files/grimmspcom2007.pdf.

(Continued)

*Primary Examiner* — Martin Lerner
(74) *Attorney, Agent, or Firm* — Lindauer Law, PLLC

(57) ABSTRACT

A wearable device includes various sensors including a microphone, heart rate monitor, pressure sensor, and so forth. The user can set the device to acquire audio data of their speech. For example, if the pressure sensor indicates the device is being worn and the user's heart rate exceeds a threshold value, audio data may be acquired. Onboard the device the audio data is processed in various ways such as detecting whether the audio data includes speech, applying a beamforming algorithm, compressing and encrypting the audio, and so forth. The audio data may be processed onboard the device, sent to another device, or a combination thereof for processing to determine sentiment data indicative of perceived emotional content of the speech. A user interface provides the user with information based on the sensor data, sentiment data, and so forth.

21 Claims, 8 Drawing Sheets

First SoC 128
Second SoC 142
Acquire first audio data from two or more microphones 402
Determine, using a first voice activity detector, second audio data from the first audio data 404
Send the second audio data to a Second SoC 406
Determine, using a beamforming algorithm, third audio from the second audio data 408
Determine, using a second voice activity detector, fourth audio data from the third audio data 410
Compress the fourth audio data to produce fifth audio data 412
Encrypt the fifth audio data to produce sixth audio data 414
Store the sixth audio data 416
Send the sixth audio data to a general processor 418
Send the sixth audio data to an external computing device 420

(51) Int. Cl.
*G06F 13/42* (2006.01)
*G10L 25/93* (2013.01)

(56) References Cited

U.S. PATENT DOCUMENTS

2008/0317259 A1* 12/2008 Zhang .................... G10L 15/04
2011/0208520 A1* 8/2011 Lee ........................ G10L 25/78
2012/0232430 A1* 9/2012 Boissy ................. A61B 5/1118 600/595
2013/0163781 A1* 6/2013 Thyssen ................. G10L 25/51
2014/0063054 A1* 3/2014 Osterhout .............. G06F 3/011 345/633
2014/0164611 A1* 6/2014 Molettiere ........... A61B 5/1118 709/224
2014/0278220 A1* 9/2014 Yuen ..................... A61B 5/681 702/150
2016/0203816 A1* 7/2016 Deng ..................... G10L 15/00 704/275
2016/0232923 A1* 8/2016 Lassche ................. G10L 25/84
2017/0169191 A1* 6/2017 Bowers ............... A61B 5/4833
2018/0174583 A1* 6/2018 Zhao ...................... G10L 25/78

OTHER PUBLICATIONS

Kehrein, Roland, "The Prosody of Authentic Emotions", ResearchGate, 10.1055/s-2003-40251, vol. 27, Jan. 1, 2001, 5 pgs. Retrieved from the Internet: URL: https://www.researchgate.net/publication/247957421_The_prosody_of_authentic_emotions.

Rozgic, et al., "Emotion Recognition using Acoustic and Lexical Features", Interspeech 2012, 13th Annual Conference of the International Speech Communication Association, Sep. 2012, 4 pgs. Retrieved from the Internet: URL: chrome-extension://efaidnbmnnnibpcajpcglclefindmkaj/https://isca-speech.org/archive_v0/archive_papers/interspeech_2012/i12_0366.pdf.

* cited by examiner 608
804
828
832
804
610
806
802
826
116(6)
858
830
812
822
860(2)
708
514(2)
824
860(1)
814
820
808
514(1)
818
818
116(6)
710
810
802
806
D1
D2

MULTI-SENSOR WEARABLE DEVICE WITH AUDIO PROCESSING

BACKGROUND

A wearable device is useful to acquire information throughout the day about a user's well-being.

BRIEF DESCRIPTION OF FIGURES

The detailed description is set forth with reference to the accompanying figures. In the figures, the left-most digit(s) of a reference number identifies the figure in which the reference number first appears. The use of the same reference numbers in different figures indicates similar or identical items or features.

Figure 1:
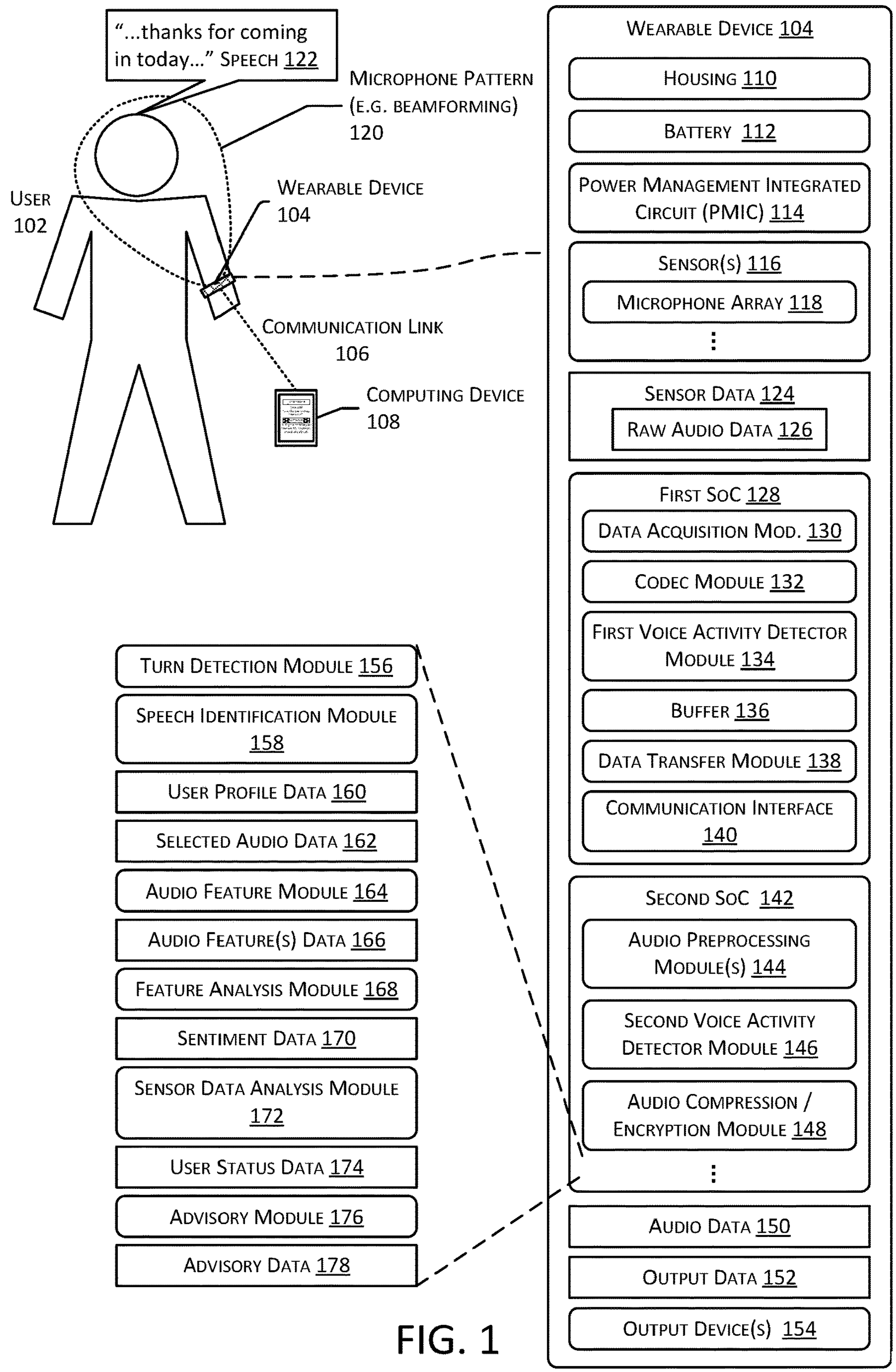
FIG. 1 is an illustrative system that includes a wearable device that includes various sensors including a microphone array that is used to acquire speech of a user, according to one implementation.

While implementations are described herein by way of example, those skilled in the art will recognize that the implementations are not limited to the examples or figures described. It should be understood that the figures and detailed description thereto are not intended to limit implementations to the particular form disclosed but, on the contrary, the intention is to cover all modifications, equivalents, and alternatives falling within the spirit and scope as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean "including, but not limited to".

The structures depicted in the following figures are not necessarily according to scale. Furthermore, the proportionality of one component to another may change with different implementations. In some illustrations the scale or a proportionate size of one structure may be exaggerated with respect to another to facilitate illustration, and not necessarily as a limitation.

DETAILED DESCRIPTION

Providing a user with the ability to monitor their physiological condition and emotional state may help the user improve their overall well-being. A poor emotional state can directly impact a person's health, just as an illness or other health event may impact a person's emotional state. A person's emotional state may also impact others that they communicate with. For example, a person who speaks with someone in an angry tone may produce in that listener an anxious emotional response. The ability to acquire data that is then used to provide information to a user may result in substantial improvements in the well-being of the user.

Described in this disclosure is a multi-sensor wearable device that includes audio processing capabilities. The user authorizes the system to acquire data using the sensors, which may include acquiring and processing the speech of the user. For example, the user may enroll to use the wearable device, and consents to acquisition and processing of audio of the user speaking. In another example, the user may operate a control on the wearable device to initiate acquisition of speech.

The sensors may include a pressure sensor that provides data to determine whether the wearable device is properly fitted to the user, a temperature sensor that provides data about the user's body temperature, accelerometers and gyroscopes that provide data about the user's movement, a heart rate monitor that provides data on the user's cardiovascular system, and the microphones that acquire the audio data of the user speaking. The audio data may then be assessed to determine sentiment data while data from the other sensors may be used to determine user status data.

The wearable device may perform various processing functions. For example, voice activity detectors may be used to determine if there is speech in a given portion of audio data, a beamforming algorithm may be used to improve the signal to noise ratio (SNR) of the speech in the audio data, audio data may be compressed, encrypted, and so forth. In one implementation the wearable device may send compressed and encrypted audio data to another device, such as a smartphone or server, for further processing to determine the sentiment data. In another implementation, the wearable device may generate the sentiment data.

The wearable device may also provide other functionality. For example, the wearable device may provide audio of the user to another device to facilitate a phone call. In another example, the user may trigger the wearable device to store audio data for notetaking purposes.

The wearable device may utilize at least two systems on a chip (SoC). For example, a first SoC may perform general tasks such as acquisition of the audio data using the microphones, scheduling when to transfer data, managing communication with other devices, and so forth. A second SoC may be used to provide more computational intensive functions such as the beamforming algorithm, compression of the audio data, encryption of the audio data, and so forth. Overall power consumption in the device is reduced and overall runtime of the wearable device between charges is increased by controlling when the second SoC is used. For example, the second SoC may be in a low power mode until the first SoC signals that there is audio data for processing. The first SoC may implement a first voice activity detection algorithm that attempts to determine if a portion of the audio data is representative of speech. If so, that portion of the audio data may be stored, and the second SoC may be powered up to a normal operating state. That stored audio data may then be sent to the second SoC which may implement a second voice activity detection algorithm that attempts to determine if some portion of that audio data is representative of human speech. If so, the second SoC may further process that portion of the audio data.

As described above, the data from the sensors on the wearable device may be used to determine sentiment data and user status data. This data may be processed and used to provide information to the user using an output device on the wearable device, a smartphone, or other device. For example, if the user's pulse exceeds a threshold value and the sentiment data indicates they are upset, a notification may be presented on a smartphone that is in communication with the wearable device.

By acquiring sensor data over extended periods of time, the wearable device provides data that may be used to inform the activities of the user and help them improve their well-being. For example, the user may be provided with advisories in a user interface. These advisories may help a user to regulate their activity, provide feedback to make healthy lifestyle changes, and maximize the quality of their health.

Illustrative System

The user 102 may have one or more wearable devices 104 on or about their person. The wearable device 104 may be implemented in various physical form factors including, but not limited to, the following: hats, headbands, necklaces, pendants, brooches, torcs, armlets, brassards, bracelets, wristbands, and so forth. In this illustration, the wearable device 104 is depicted as a wristband.

The wearable device 104 may use an interface to establish a communication link 106 to maintain communication with a computing device 108. For example, the computing device 108 may include a phone, tablet computer, personal computer, server, internet enabled device, voice activated device, smart-home device, and so forth. The communication link 106 may implement at least a portion of one or more of the Bluetooth Classic specification, Bluetooth Low Energy specification, and so forth.

The wearable device 104 includes a housing 110. A battery 112 or other power storage or generation device may be arranged within the housing 110. For example, the battery 112 may comprise a rechargeable battery.

The wearable device 104 includes a power management integrated circuit (PMIC) 114. The PMIC 114 may provide various functions such as controlling the charging of the battery 112, providing appropriate electrical power to other components in the wearable device 104, and so forth.

The wearable device 104 includes one or more sensors 116, such as a microphone array 118. For example, the microphone array 118 may comprise two or more microphones arranged to acquire sound from ports at different locations through the housing 110. As described below, a microphone pattern 120 may provide gain or directivity using a beamforming algorithm. Speech 122 by the user 102 or other sources within range of the microphone array 118 may be detected by the microphone array 118 and raw audio data 126 may be acquired. In other implementations raw audio data 126 may be acquired from other devices. The sensors 116 are discussed in more detail with regard to FIG. 2.

In one implementation, an additional processor (not shown) may be used to process the raw audio data 126 from the microphone array 118. For example, a neural network may be trained to recognize the speech of the user 102. The raw audio data 126 that is not deemed to be from the user 102 may be discarded. In this implementation, the raw audio data 126 may then comprise audio associated with the user 102. This functionality may operate in conjunction with, or instead of, the speech identification module 158 described below.

The wearable device 104 includes a first system on a chip (SoC) 128. The first SoC 128 may include, in a single package various, components including one or more processors or "cores", memory, communication interfaces, input/output ports, and so forth. For example, the first SoC 128 may comprise the RTL8763 SoC from Realtek Semiconductor Corp. of Hsinchu, Taiwan. While the implementations depicted here describe SoC arrangements, other arrangements may be used. For example, several discrete components may be interconnected to provide the same functionality.

The first SoC 128 may provide various functions. A data acquisition module 130 may comprise instructions stored in the memory that execute on the processor(s) of the first SoC 128 to acquire sensor data 124 from one or more sensors 116, and so forth.

The first SoC 128 may include a codec module 132. The codec module 132 may include an analog to digital converter (ADC) that accepts analog input from the microphones in the microphone array 118 and produces a digitized stream of audio data. For example, the codec module 132 may provide as output 16 bit audio data with a sample rate of 16 kilohertz.

The first SoC 128 may include a first voice activity detector module 134. The first voice activity detector module 134 may be implemented in one or more of hardware or as instructions stored in the memory and executed on the processor(s). The first voice activity detector module 134 determines if a portion of the audio data from the codec module 132 is representative of speech 122. For example, the microphone array 118 may obtain raw audio data 126 that contains ambient noises such as traffic, wind, and so forth. Raw audio data 126 that is not deemed to contain speech 122 may be discarded. Resource consumption is minimized by discarding raw audio data 126 that does not contain speech 122. For example, power consumption, demands for memory and computational resources, communication bandwidth, and so forth are minimized by limiting further processing of raw audio data 126 determined to not likely contain speech 122.

The first voice activity detector module 134 may use one or more techniques to determine voice activity. For example, characteristics of the signals present in the raw audio data 126 such as frequency, energy, zero-crossing rate, and so forth may be analyzed with respect to threshold values to determine characteristics that are deemed likely to be human speech.

The portion of the raw audio data 126 that is determined by the first voice activity detector module 134 to contain speech 122 may be stored in a buffer 136 in the first SoC 128. A data transfer module 138 may control when audio data in the buffer 136 is sent to a second SoC 142.

The data transfer module 138 may also determine that a memory within the wearable device 104 has reached a predetermined quantity of stored audio data. The communication interface 140 may comprise a Bluetooth Low Energy device that is operated responsive to commands from the data transfer module 138 to send the stored audio data to the computing device 108.

Communication between the wearable device 104 and the computing device 108 may be persistent or intermittent. For example, the wearable device 104 may determine and store audio data while the communication link 106 to the computing device 108 is unavailable. At a later time, when the communication link 106 is available, the audio data may be sent to the computing device 108.

In some implementations, the first SoC 128 may include one or more communication interfaces 140. For example, the communication interfaces 140 may include a Bluetooth wireless communication interface, a Wi-Fi interface, a serial peripheral interface (SPI), an inter-integrated circuit sound (I2S) interface, and so forth.

The second SoC 142 may have different capabilities from the first SoC 128. The second SoC 142 may include processors, memory, or other hardware that facilitates the processing of audio data such as one or more digital signal processors, neural network processors, audio feature extraction circuitry, and so forth. For example, the second SoC 142 may comprise the Quark SoC X1000 from Intel Corporation of Santa Clara, Calif., United States of America.

The second SoC 142 may include one or more audio preprocessing module(s) 144 that are implemented in one or more of hardware or as instructions stored in the memory and executed on the processor(s). In one implementation the audio preprocessing module 144 may implement a beamforming algorithm, noise reduction algorithms, filters, and so forth. For example, the audio preprocessing module 144 may use a beamforming algorithm to provide directivity or gain and improve the signal to noise ratio (SNR) of the speech 122 from the user 102 with respect to speech 122 or noise from other sources.

The audio preprocessing module 144 may use information from one or more sensors 116 during operation. For example, sensor data 124 from an accelerometer may be used to determine orientation of the wearable device 104. Based on the orientation, the beamforming algorithm may be operated to provide a microphone pattern 120 that includes a location where the user's 102 head is expected to be.

The second SoC 142 may include a second voice activity detector module 146. The second voice activity detector module 146 may be implemented in one or more of hardware or as instructions stored in the memory and executed on the processor(s). The second voice activity detector module 146 determines if a portion of the audio data sent from the first SoC 128 is representative of speech 122. The second voice activity detector module 146 may implement one or more techniques to determine the presence of speech 122 that are different from the first voice activity detector module 134.

The second voice activity detector module 146 may use one or more techniques to determine voice activity. For example, characteristics of the signals present in the raw audio data 126 such as frequency, energy, zero-crossing rate, and so forth may be analyzed with respect to threshold values to determine characteristics that are deemed likely to be human speech.

In some implementations the same techniques may be used by the first voice activity detector module 134 and the second voice activity detector module 146, but with different sets of threshold values. For example, the first voice activity detector module 134 may use a first set of one or more threshold values during operation while the second voice activity detector module 146 may use a second set of one or more threshold values.

The second SoC 142 may also provide an audio compression and encryption module 148. The audio compression and encryption module 148 may implement Opus audio compression as promulgated by opus-codec.org. Encryption may utilize a public key/private key infrastructure. In other implementations these functions may be performed by separate modules, different hardware, and so forth.

The audio data that is not determined to contain speech 122 by the second voice activity detector module 146 may discarded. Resource consumption is minimized by discarding the audio data that does not contain speech 122. For example, power consumption, demands for memory and computational resources, communication bandwidth, and so forth are minimized by limiting further processing of raw audio data 126 determined to not likely contain speech 122.

During operation, the second SoC 142 produces audio data 150 that is highly likely to contain speech 122. Compared to the raw audio data 126, the speech 122 in the audio data 150 may exhibit a greater SNR, have less overall noise, may be compressed, and may also be encrypted.

The second SoC 142 may then store the audio data 150 for further processing on the wearable device 104 or for transmission to another device. The further processing may include determining the sentiment data. For example, the audio data 150 may be sent to the computing device 108.

The determination of the sentiment data may comprise determining the portion of the audio data 150 that is associated with the user 102 specifically and processing that portion as described below.

The wearable device 104 may determine output data 152. In one implementation, a user interface module may determine the output data 152. For example, the output data 152 may comprise hypertext markup language (HTML) instructions that, when processed by a browser engine, generate an image of a graphical user interface (GUI). In another example, the output data 152 may comprise an instruction to play a particular sound, operate a buzzer, or operate a light to present a particular color at a particular intensity.

The output data 152 may then be used to operate one or more output devices 154. Continuing the examples, the GUI may be presented on a display device, a buzzer may be operated, the light may be illuminated, and so forth to provide output. The output may include a user interface, such as the GUI depicted here that provides information about the sentiment for yesterday and the previous hour, information about pulse rate, and so forth. The sentiment may be presented as an indication with respect to a typical range of sentiment associated with the user 102.

In some implementations the wearable device 104 may send one or more of the audio data 150 or the sensor data 124 to another device for processing. For example, the audio data 150 may be sent to the computing device 108 using a Bluetooth wireless communication interface. In other implementations the processing and other operations may be performed on the wearable device 104 by one or more of the first SoC 128 or the second SoC 142. The modules described in this disclosure may be implemented using one or more of dedicated hardware, programmable hardware, instructions executing on a processor, and so forth.

A turn detection module 156 may determine that portions of the audio data 150 are associated with different speakers. When more than one person is speaking, a "turn" is a contiguous portion of speech by a single person. For example, a first turn may include several sentences spoken by a first person, while a second turn includes a response by a second person. The turn detection module 156 may use one or more characteristics in the audio data 150 to determine that a turn has taken place. For example, a turn may be detected based on a pause in speech 122, change in pitch, change in signal amplitude, and so forth. Continuing the example, if the pause between words exceeds 350 milliseconds, data indicative of a turn may be determined.

In one implementation the turn detection module 156 may process segments of the audio data 150 to determine if the person speaking at the beginning of the segment is the same as the person speaking at the end. The audio data 150 may be divided into segments and subsegments. For example, each segment may be six seconds long with a first subsegment that includes a beginning two seconds of the segment and a second subsegment that includes the last two seconds of the segment. The data in the first subsegment is processed to determine a first set of features and the data in the second subsegment is processed to determine a second set of features. Segments may overlap, such that at least some data is duplicated between successive segments. If the first set of features and the second set of features are determined to be within a threshold value of one another, they may be deemed to have been spoken by the same person. If the first set of features and the second set of features are not within the threshold value of one another, they may be deemed to have been spoken by different people. A segment that includes speech from two different people may be designated as a break between one speaker and another. In this implementation, those breaks between speakers may be used to determine the boundaries of a turn. For example, a turn may be determined to begin and end when a segment includes speech from two different people.

In some implementations the turn detection module 156 may operate in conjunction with, or as part of, a speech identification module 158, as described below. For example, if the speech identification module 158 identifies that a first segment is spoken by a first user and a second segment is spoken by a second user, data indicative of a turn may be determined.

The speech identification module 158 may access user profile data 160 to determine if the audio data 150 is associated with the user 102. For example, user profile data 160 may comprise information about speech 122 provided by the user 102 during an enrollment process. During enrollment, the user 102 may provide a sample of their speech 122 which is then processed to determine features that may be used to identify if speech 122 is likely to be from that user 102.

The speech identification module 158 may process at least a portion of the audio data 150 that is designated as a particular turn to determine if the user 102 is the speaker. For example, the audio data 150 of the first turn may be processed by the speech identification module 158 to determine a confidence level of 0.97 that the first turn is the user 102 speaking. A threshold confidence value of 0.95 may be specified. Continuing the example, the audio data 150 of the second turn may be processed by the speech identification module 158 that determines a confidence level of 0.17 that the second turn is the user 102 speaking.

Selected audio data 162 is determined that comprises the portion(s) of the audio data 150 that is determined to be speech 122 from the user 102. For example, the selected audio data 162 may consist of the speech 122 which exhibits a confidence level greater than the threshold confidence value of 0.95. As a result, the selected audio data 162 omits speech 122 from other sources, such as someone who is in conversation with the user 102.

An audio feature module 164 uses the selected audio data 162 to determine audio feature data 166. For example, the audio feature module 164 may use one or more systems such as signal analysis, classifiers, neural networks, and so forth to generate the audio feature data 166. The audio feature data 166 may comprise values, vectors, and so forth. For example, the audio feature module 164 may use a convolutional neural network that accepts as input the selected audio data 162 and provides as output vectors in a vector space. The audio feature data 166 may be representative of features such as rising pitch over time, speech cadence, energy intensity per phoneme, duration of a turn, and so forth.

A feature analysis module 168 uses the audio feature data 166 to determine sentiment data 170. Human speech involves a complex interplay of biological systems on the part of the person speaking. These biological systems are affected by the physical and emotional state of the person. As a result, the speech 122 of the user 102 may exhibit changes. For example, a person who is calm sounds different from a person who is excited. This may be described as "emotional prosody" and is separate from the meaning of the words used. For example, in some implementations the feature analysis module 168 may use the audio feature data 166 to assess emotional prosody without assessment of the actual content of the words used.

The feature analysis module 168 determines the sentiment data 170 that is indicative of a possible emotional state of the user 102 based on the audio feature data 166. The feature analysis module 168 may determine various values that are deemed to be representative of emotional state. In some implementations these values may be representative of emotional primitives. (See Kehrein, Roland. (2002). The prosody of authentic emotions. 27. 10.1055/s-2003-40251.) For example, the emotional primitives may include valence, activation, and dominance. A valence value may be determined that is representative of a particular change in pitch of the user's voice over time. Certain valence values indicative of particular changes in pitch may be associated with certain emotional states. An activation value may be determined that is representative of pace of the user's speech over time. As with valence values, certain activation values may be associated with certain emotional states. A dominance value may be determined that is representative of rise and fall patterns of the pitch of the user's voice overtime. As with valence values, certain dominance values may be associated with certain emotional states. Different values of valence, activation, and dominance may correspond to particular emotions. (See Grimm, Michael (2007). Primitives-based evaluation and estimation of emotions in speech. Speech Communication 49 (2007) 787-800.)

Other techniques may be used by the feature analysis module 168. For example, the feature analysis module 168 may determine Mel Frequency Cepstral Coefficients (MFCC) of at least a portion of the selected audio data 162. The MFCC may then be used to determine an emotional class associated with the portion. The emotional class may include one or more of angry, happy, sad, or neutral. (See Rozgic, Viktor, et. al, (2012). Emotion Recognition using Acoustic and Lexical Features. 13th Annual Conference of the International Speech Communication Association 2012, INTERSPEECH 2012. 1.)

In other implementations the feature analysis module 168 may include analysis of the words spoken and their meaning. For example, an automated speech recognition (ASR) system may be used to determine the text of the words spoken. This information may then be used to determine the sentiment data 170. For example, presence in the selected audio data 162 of words that are associated with a positive connotation, such as compliments or praise, may be used to determine the sentiment data 170. In another example, word stems may be associated with particular sentiment categories. The word stems may be determined using ASR, and the particular sentiment categorizes determined. (See Rozgic, Viktor, et. al, (2012). Emotion Recognition using Acoustic and Lexical Features. 13th Annual Conference of the International Speech Communication Association 2012, INTERSPEECH 2012. 1.) Other techniques may be used to determine emotional state based at least in part on the meaning of words spoken by the user.

The sentiment data 170 determined by the feature analysis module 168 may be expressed as one or more numeric values, vectors, words, and so forth. For example, the sentiment data 170 may comprise a composite single value, such as a numeric value, color, and so forth. For example, a weighted sum of the valence, activation, and dominance values may be used to generate an overall sentiment index or "tone value" or "mood value". In another example, the sentiment data 170 may comprise one or more vectors in an n-dimensional space. In yet another example, the sentiment data 170 may comprise associated words that are determined by particular combinations of other values, such as valence, activation, and dominance values. The sentiment data 170 may comprise values that are non-normative. For example, a sentiment value that is expressed as a negative number may not be representative of an emotion that is considered to be bad.

In some implementations the feature analysis module 168 may consider other sensor data 124 as well. Information such as heart rate, respiration rate, blood pressure, and so forth may be combined and used to determine the sentiment data 170. For example, a cardiac pulse of the user 102 that is above a threshold value may contribute to a determination of sentiment data 170 indicative of "under stress".

A sensor data analysis module 172 may also be used. The sensor data analysis module 172 may process the sensor data 124 and generate user status data 174. For example, the sensor data 124 obtained from sensors 116 on the wearable device 104 may comprise information about movement obtained from an accelerometer(s) or gyroscope(s), body temperature, pulse rates obtained from a heart rate monitor, and so forth. The user status data 174 may comprise information such as core body temperature, count of steps, classification of activity based on movement, energy expenditure based on movement, heart rate monitoring, heart rate variability, stress monitoring, sleep monitoring, and so forth. The user status data 174 may provide information that is representative of the physiological state of the user 102.

An advisory module 176 may use the sentiment data 170 and the user status data 174 to determine advisory data 178. The sentiment data 170 and the user status data 174 may each include timestamp information. Sentiment data 170 for a first time period may be associated with user status data 174 for a second time period. Historical data may be used to determine trends. These trends may then be used by the advisory module 176 to determine advisory data 178. For example, trend data may indicate that when the user status data 174 indicates that the user 102 sleeps for fewer than 7 hours per night, the following day their overall tone value is below their personal baseline value. As a result, the advisory module 176 may generate advisory data 178 to inform the user 102 of this and suggest more rest.

In some implementations the advisory data 178 may include speech recommendations. These speech recommendations may include suggestions as to how the user 102 may manage their speech to change or moderate the apparent emotion presented by their speech. In some implementations, the speech recommendations may advise the user 102 to speak more slowly, pause, breath more deeply, suggest a different tone of voice, and so forth. For example, if the sentiment data 170 indicates that the user 102 appears to have been upset, the advisory data 178 may be for the user 102 to stop speaking for ten seconds and then continue speaking in a calmer voice. In some implementations the speech recommendations may be associated with particular goals. For example, the user 102 may wish to sound more assertive and confident. The user 102 may provide input that indicates these goals, with that input used to set minimum threshold values for use by the advisory module 176. The advisory module 176 may analyze the sentiment data 170 with respect to these minimum threshold values to provide the advisory data 178. Continuing the example, if the sentiment data 170 indicates that the speech of the user 102 was below the minimum threshold values, the advisory data 178 may inform the user 102 and may also suggest actions.

The computing device 108 may generate output data 152 from one or more of the sentiment data 170 or the advisory data 178. For example, the output data 152 may comprise hypertext markup language (HTML) instructions that, when processed by a browser engine, generate an image of a graphical user interface (GUI). In another example, the output data 152 may comprise an instruction to play a particular sound, operate a buzzer, or operate a light to present a particular color at a particular intensity.

The output data 152 may then be used to operate one or more output devices 154. Continuing the examples, the GUI may be presented on a display device, a buzzer may be operated, the light may be illuminated, and so forth to provide output. The output may include a user interface, such as the GUI depicted here that provides information about the sentiment for yesterday and the previous hour using several interface elements. In this example, the sentiment is presented as an indication with respect to a typical range of sentiment associated with the user 102. In some implementations the sentiment may be expressed as numeric values and interface elements with particular colors associated with those numeric values may be presented in the user interface. For example, if the sentiment of the user 102 has one or more values that exceed the user's 102 typical range for a metric associated with being happy, an interface element colored green may be presented. In contrast, if the sentiment of the user 102 has one or more values that are below the user's 102 typical range, an interface element colored blue may be presented. The typical range may be determined using one or more techniques. For example, the typical range may be based on minimum sentiment values, maximum sentiment values, may be specified with respect to an average or linear regression line, and so forth.

The system may provide output based on data obtained over various time intervals. For example, the user interface illustrates sentiment for yesterday and the last hour. The system 100 may present information about sentiment associated with other periods of time. For example, the sentiment data 170 may be presented on a real time or near-real time basis using raw audio data 126 obtained in the last n seconds, where n is greater than zero.

It is understood that the various functions, modules, and operations described in this system 100 may be performed by other devices. For example, the advisory module 176 may execute on a server.

The wearable device 104 may operate in a variety of different modes. A first mode involves the wearable device 104 acquiring raw audio data 126 and determining sentiment data 170 continuously.

A second mode involves the wearable device 104 automatically acquiring raw audio data 126 and generating corresponding sentiment data 170 for sampled periods of time. For example, a 3.5 minute sample of raw audio data 126 may be obtained every 30 minutes during a 16 hour waking day. Meanwhile the user status data 174 is determined continuously. For example, information such as temperature, acceleration, and so forth may be sampled continuously throughout the day at particular intervals, upon a triggering event, and so forth.

A third mode involves user 102 scheduled acquisition of the raw audio data 126. For example, the user 102 may manually initiate acquisition of the raw audio data 126 by pressing a button, using the computing device 108 to set a schedule in advance for a meeting, and so forth. Meanwhile the user status data 174 is determined continuously. For example, information such as temperature, acceleration, and so forth may be sampled continuously throughout the day at particular intervals, upon a triggering event, and so forth.

A fourth mode involves the acquisition of user status data 174 only. The user status data 174 is determined continuously. For example, information such as temperature, acceleration, and so forth may be sampled continuously throughout the day at particular intervals, upon a triggering event, and so forth. No raw audio data 126 is acquired.

In other implementations other hardware configurations may be used. For example, a single SoC may include different cores, signal processors, neural networks, or other components and may perform the functions described with regard to the first SoC 128 and the second SoC 142.

In some implementations, the audio feature data 166 may be determined by the components on the wearable device 104 and then sent via the communication link 106 to the computing device 108. The computing device 108 may then determine the sentiment data 170 or perform other functions.

Figure 2:
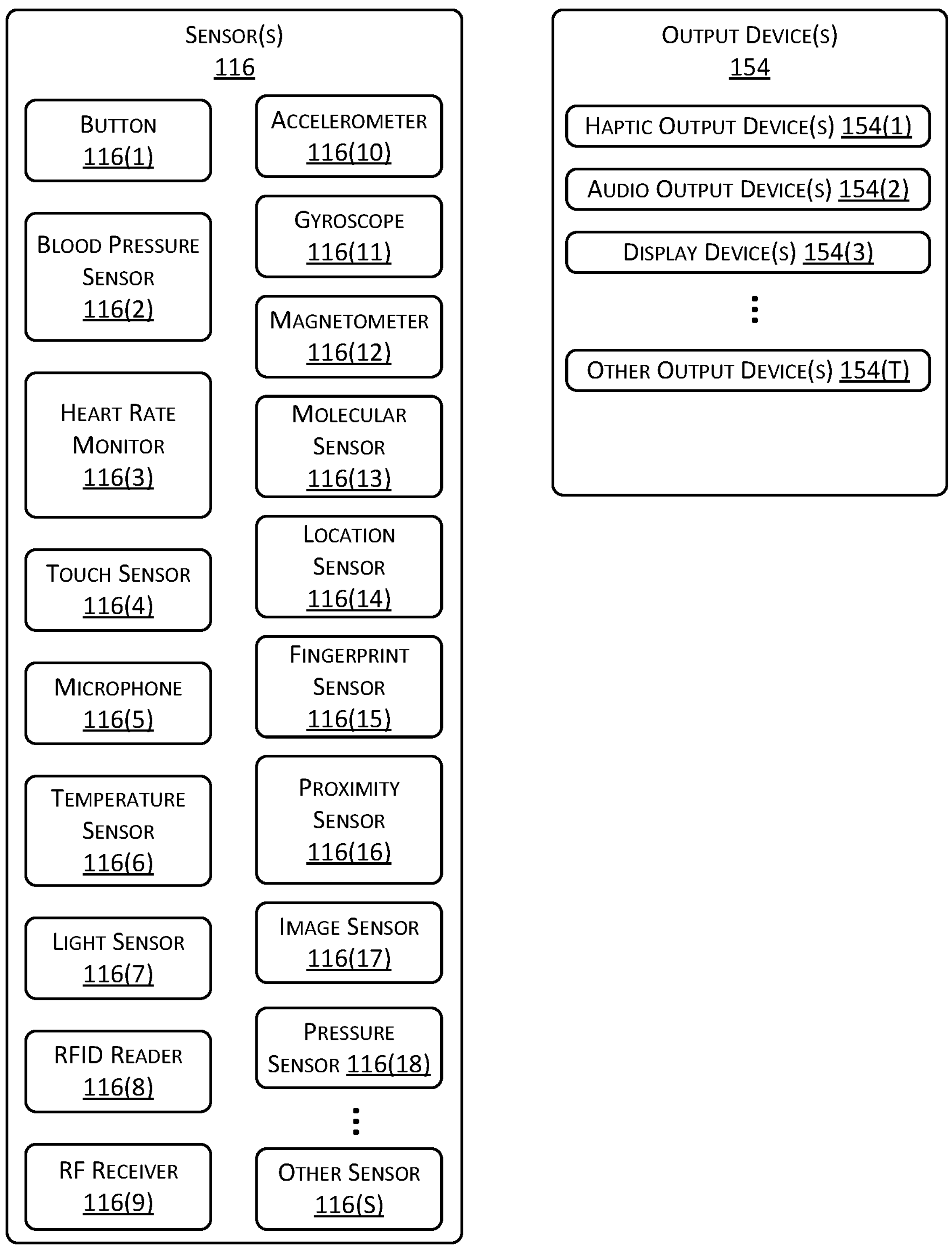
FIG. 2 illustrates a block diagram of sensors and output devices that may be used during operation of the system, according to one implementation.

FIG. 2 illustrates a block diagram 200 of sensors 116 and output devices 154 that may be used by the wearable device 104, the computing device 108, or other devices during operation of the system 100, according to one implementation. As described above with regard to FIG. 1, the sensors 116 may generate sensor data 124.

The one or more sensors 116 may be integrated with or internal to a computing device, such as the wearable device 104, the computing device 108, and so forth. For example, the sensors 116 may be built-in to the wearable device 104 during manufacture. In other implementations, the sensors 116 may be part of another device. For example, the sensors 116 may comprise a device external to, but in communication with, the computing device 108 or the wearable device 104 using Bluetooth, Wi-Fi, 3G, 4G, LTE, ZigBee, Z-Wave, or another wireless or wired communication technology.

The one or more sensors 116 may include one or more buttons 116(1) that are configured to accept input from the user 102. The buttons 116(1) may comprise mechanical, capacitive, optical, or other mechanisms. For example, the buttons 116(1) may comprise mechanical switches configured to accept an applied force from a touch of the user 102 to generate an input signal. In some implementations input from one or more sensors 116 may be used to initiate acquisition of the raw audio data 126. For example, activation of a button 116(1) may initiate acquisition of the raw audio data 126.

A blood pressure sensor 116(2) may be configured to provide sensor data 124 that is indicative of the user's 102 blood pressure. For example, the blood pressure sensor 116(2) may comprise a camera that acquires images of blood vessels and determines the blood pressure by analyzing the changes in diameter of the blood vessels over time. In another example, the blood pressure sensor 116(2) may comprise a sensor transducer that is in contact with the skin of the user 102 that is proximate to a blood vessel.

A heart rate monitor 116(3) may be configured to provide sensor data 124 that is indicative of a cardiac pulse rate. For example, the heart rate monitor 116(3) may operate as a photoplethysmograph (PPG). Heart rate variability may be determined, based on changes to the cardiac pulse rate over time. In some implementations other data such as oxygen saturation of the user's 102 blood, respiration rate, and so forth may also be determined. The heart rate monitor 116(3) may use one or more light emitting diodes (LEDs) and corresponding detectors to determine changes in apparent color of the blood of the user 102 resulting from oxygen binding with hemoglobin in the blood, providing information about the presence of blood, oxygen saturation, perfusion, and so forth. Changes over time in apparent reflectance of light emitted by the LEDs may be used to determine data such as cardiac pulse. In one implementation the heart rate monitor 116(3) may comprise a MAX86141 from Maxim Integrated, Inc. of San Jose, Calif., United States of America.

The heart rate monitor 116(3) may comprise a multicolor light emitting diode (LED), a first photodiode, a green LED, and a second photodiode that are arranged proximate to a sensor window. During normal operation, the sensor window is either in contact with or near the skin of the user 102. During operation, one or more of the LED's may be operated to illuminate a portion of the user 102. One or more of the photodiodes may be used to detect the light from the illumination which has interacted with the body of the user 102. The placement and arrangement of the components of the heart rate monitor 116(3) are depicted below with regard to FIG. 8.

The sensors 116 may include one or more touch sensors 116(4). The touch sensors 116(4) may use resistive, capacitive, surface capacitance, projected capacitance, mutual capacitance, optical, Interpolating Force-Sensitive Resistance (IFSR), or other mechanisms to determine the position of a touch or near-touch of the user 102. For example, the IFSR may comprise a material configured to change electrical resistance responsive to an applied force. The location within the material of that change in electrical resistance may indicate the position of the touch.

One or more microphones 116(5) may be configured to acquire information about sound present in the environment. In some implementations, a plurality of microphones 116(5) may be used to form the microphone array 118. As described above, the microphone array 118 may implement beamforming techniques to provide for directionality of gain.

A temperature sensor (or thermometer) 116(6) may provide information indicative of a temperature of an object. For example, the temperature sensor 116(6) may comprise an AS6200 from ams AG of Unterpremstatten, Styria, Austria. The temperature sensor 116(6) may be configured to measure ambient air temperature proximate to the user 102, the body temperature of the user 102, and so forth. The temperature sensor 116(6) may comprise a silicon bandgap temperature sensor, thermistor, thermocouple, or other device. In some implementations, the temperature sensor 116(6) may comprise an infrared detector configured to determine temperature using thermal radiation. In one implementation, the temperature sensor 116(6) used to determine the body temperature of the user 102 may be located proximate to a bottom surface of a housing of the wearable device 104. The temperature sensor 116(6) used to determine the ambient temperature may be located proximate to a top surface of the wearable device 104.

The sensors 116 may include one or more light sensors 116(7). The light sensors 116(7) may be configured to provide information associated with ambient lighting conditions such as a level of illumination. The light sensors

116(7) may be sensitive to wavelengths including, but not limited to, infrared, visible, or ultraviolet light. In contrast to a camera, the light sensor 116(7) may typically provide a sequence of amplitude (magnitude) samples and color data while the camera provides a sequence of two-dimensional frames of samples (pixels).

One or more radio frequency identification (RFID) readers 116(8), near field communication (NFC) systems, and so forth, may also be included as sensors 116. The user 102, objects, locations within a building, and so forth, may be equipped with one or more radio frequency (RF) tags. The RF tags are configured to emit an RF signal. In one implementation, the RF tag may be a RFID tag configured to emit the RF signal upon activation by an external signal. For example, the external signal may comprise a RF signal or a magnetic field configured to energize or activate the RFID tag. In another implementation, the RF tag may comprise a transmitter and a power source configured to power the transmitter. For example, the RF tag may comprise a Bluetooth Low Energy (BLE) transmitter and a battery. In other implementations, the tag may use other techniques to indicate its presence. For example, an acoustic tag may be configured to generate an ultrasonic signal, which is detected by corresponding acoustic receivers. In yet another implementation, the tag may be configured to emit an optical signal.

One or more RF receivers 116(9) may also be included as sensors 116. In some implementations, the RF receivers 116(9) may be part of transceiver assemblies. The RF receivers 116(9) may be configured to acquire RF signals associated with Wi-Fi, Bluetooth, ZigBee, Z-Wave, 3G, 4G, LTE, or other wireless data transmission technologies. The RF receivers 116(9) may provide information associated with data transmitted via radio frequencies, signal strength of RF signals, and so forth. For example, information from the RF receivers 116(9) may be used to facilitate determination of a location of the device, and so forth.

The sensors 116 may include one or more accelerometers 116(10). The accelerometers 116(10) may provide information such as the direction and magnitude of an imposed acceleration, tilt relative to local vertical, and so forth. Data such as rate of acceleration, determination of changes in direction, speed, tilt, and so forth, may be determined using the accelerometers 116(10). For example, the accelerometer 116(10) and the gyroscope 116(11) may be combined in an inertial measurement unit (IMU), such as an ST Micro LSM6DSL device from ST Microelectronics NV of Schiphol, Amsterdam, Netherlands.

Data from the accelerometers 116(10) may be used to detect user input. For example, a user 102 may tap the wearable device 104. For example, two taps may be used to provide a readout of battery charge available, three taps may be used to turn on Bluetooth and initiate the Bluetooth pairing process, and so forth.

A gyroscope 116(11) or gyrometer provides information indicative of rotation of an object affixed thereto. For example, the gyroscope 116(11) may indicate whether the device has been rotated.

A magnetometer 116(12) may be used to determine an orientation by measuring ambient magnetic fields, such as the terrestrial magnetic field. For example, output from the magnetometer 116(12) may be used to determine whether the device containing the sensor 116 has changed orientation or otherwise moved. In other implementations, the magnetometer 116(12) may be configured to detect magnetic fields generated by another device.

A molecular sensor 116(13) may be used to determine a concentration of one or more molecules such as water, glucose, and so forth within the blood or tissues of the user 102. For example, the molecular sensor 116(13) may comprise a near infrared spectroscope that determines a concentration of glucose or glucose metabolites in tissues. In another example, the molecular sensor 116(13) may comprise a chemical detector that measures presence of one or more types of molecules at the surface of the user's 102 skin. In still another implementation, the molecular sensor 116 (13) may comprise a radio frequency transmitter, a radio receiver, and one or more antennas. A radio frequency (RF) signal may be emitted into a portion of the user 102. As the RF signal interacts with one or more different types of molecules, changes in signal characteristics such as amplitude, phase, and so forth may be detected by the radio receiver. Information about the presence, concentration, and so forth of particular molecules may be determined based on the received RF signal.

A location sensor 116(14) is configured to provide information indicative of a location. The location may be relative or absolute. For example, a relative location may indicate "kitchen", "bedroom", "conference room", and so forth. In comparison, an absolute location is expressed relative to a reference point or datum, such as a street address, geolocation comprising coordinates indicative of latitude and longitude, grid square, and so forth. The location sensor 116(14) may include, but is not limited to, radio navigation-based systems such as terrestrial or satellite-based navigational systems. The satellite-based navigation system may include one or more of a Global Positioning System (GPS) receiver, a Global Navigation Satellite System (GLONASS) receiver, a Galileo receiver, a BeiDou Navigation Satellite System (BDS) receiver, an Indian Regional Navigational Satellite System, and so forth. In some implementations, the location sensor 116(14) may be omitted or operate in conjunction with an external resource such as a cellular network operator providing location information, or Bluetooth beacons.

A fingerprint sensor 116(15) is configured to acquire fingerprint data. The fingerprint sensor 116(15) may use an optical, ultrasonic, capacitive, resistive, or other detector to obtain an image or other representation of features of a fingerprint. For example, the fingerprint sensor 116(15) may comprise a capacitive sensor configured to generate an image of the fingerprint of the user 102.

A proximity sensor 116(16) may be configured to provide sensor data 124 indicative of one or more of a presence or absence of an object, a distance to the object, or characteristics of the object. The proximity sensor 116(16) may use optical, electrical, ultrasonic, electromagnetic, or other techniques to determine a presence of an object. For example, the proximity sensor 116(16) may comprise a capacitive proximity sensor configured to provide an electrical field and determine a change in electrical capacitance due to presence or absence of an object within the electrical field.

An image sensor 116(17) comprises an imaging element to acquire images in visible light, infrared, ultraviolet, and so forth. For example, the image sensor 116(17) may comprise a complementary metal oxide (CMOS) imaging element or a charge coupled device (CCD).

A pressure sensor 116(18) may provide information about the pressure between a portion of the wearable device 104 and a portion of the user 102. For example, the pressure sensor 116(18) may comprise a capacitive element, strain gauge, spring-biased contact switch, or other device that is used to determine pressure data indicative of the amount of pressure between the user's 102 arm and an inner surface of the wearable device 104 that is in contact with the arm. In some implementations the pressure sensor 116(18) may provide pressure data indicative of a force measurement, such as 0.5 Newtons, a relative force measurement, or whether the pressure is greater than a threshold value.

The sensors 116 may include other sensors 116(S) as well. For example, the other sensors 116(S) may include strain gauges, anti-tamper indicators, and so forth. For example, strain gauges or strain sensors may be embedded within the wearable device 104 and may be configured to provide information indicating that at least a portion of the wearable device 104 has been stretched or displaced such that the wearable device 104 may have been donned or doffed.

In some implementations, the sensors 116 may include hardware processors, memory, and other elements configured to perform various functions. Furthermore, the sensors 116 may be configured to communicate by way of a network or may couple directly with the other devices.

The wearable device 104, the computing device 108, and so forth may include or may couple to one or more output devices 154. The output devices 154 are configured to generate signals which may be perceived by the user 102, detectable by the sensors 116, or a combination thereof.

Haptic output devices 154(1) are configured to provide a signal, which results in a tactile sensation to the user 102. The haptic output devices 154(1) may use one or more mechanisms such as electrical stimulation or mechanical displacement to provide the signal. For example, the haptic output devices 154(1) may be configured to generate a modulated electrical signal, which produces an apparent tactile sensation in one or more fingers of the user 102. In another example, the haptic output devices 154(1) may comprise piezoelectric or rotary motor devices configured to provide a vibration that may be felt by the user 102.

One or more audio output devices 154(2) are configured to provide acoustic output. The acoustic output includes one or more of infrasonic sound, audible sound, or ultrasonic sound. The audio output devices 154(2) may use one or more mechanisms to generate the acoustic output. These mechanisms may include, but are not limited to, the following: voice coils, piezoelectric elements, magnetostrictive elements, electrostatic elements, and so forth. For example, a piezoelectric buzzer or a speaker may be used to provide acoustic output by an audio output device 154(2).

The display devices 154(3) may be configured to provide output that may be seen by the user 102 or detected by a light-sensitive detector such as the image sensor 116(17) or light sensor 116(7). The output may be monochrome or color. The display devices 154(3) may be emissive, reflective, or both. An emissive display device 154(3), such as using LEDs, is configured to emit light during operation. In comparison, a reflective display device 154(3), such as using an electrophoretic element, relies on ambient light to present an image. Backlights or front lights may be used to illuminate non-emissive display devices 154(3) to provide visibility of the output in conditions where the ambient light levels are low.

The display mechanisms of display devices 154(3) may include, but are not limited to, micro-electromechanical systems (MEMS), spatial light modulators, electroluminescent displays, quantum dot displays, liquid crystal on silicon (LCOS) displays, cholesteric displays, interferometric displays, liquid crystal displays, electrophoretic displays, LED displays, and so forth. These display mechanisms are configured to emit light, modulate incident light emitted from another source, or both. The display devices 154(3) may operate as panels, projectors, and so forth.

The display devices 154(3) may be configured to present images. For example, the display devices 154(3) may comprise a pixel-addressable display. The image may comprise at least a two-dimensional array of pixels or a vector representation of an at least two-dimensional image.

In some implementations, the display devices 154(3) may be configured to provide non-image data, such as text or numeric characters, colors, and so forth. For example, a segmented electrophoretic display device 154(3), segmented LED, and so forth, may be used to present information such as letters or numbers. The display devices 154(3) may also be configurable to vary the color of the segment, such as using multicolor LED segments.

Other output devices 154(T) may also be present. For example, the other output devices 154(T) may include scent dispensers.

Figure 3:
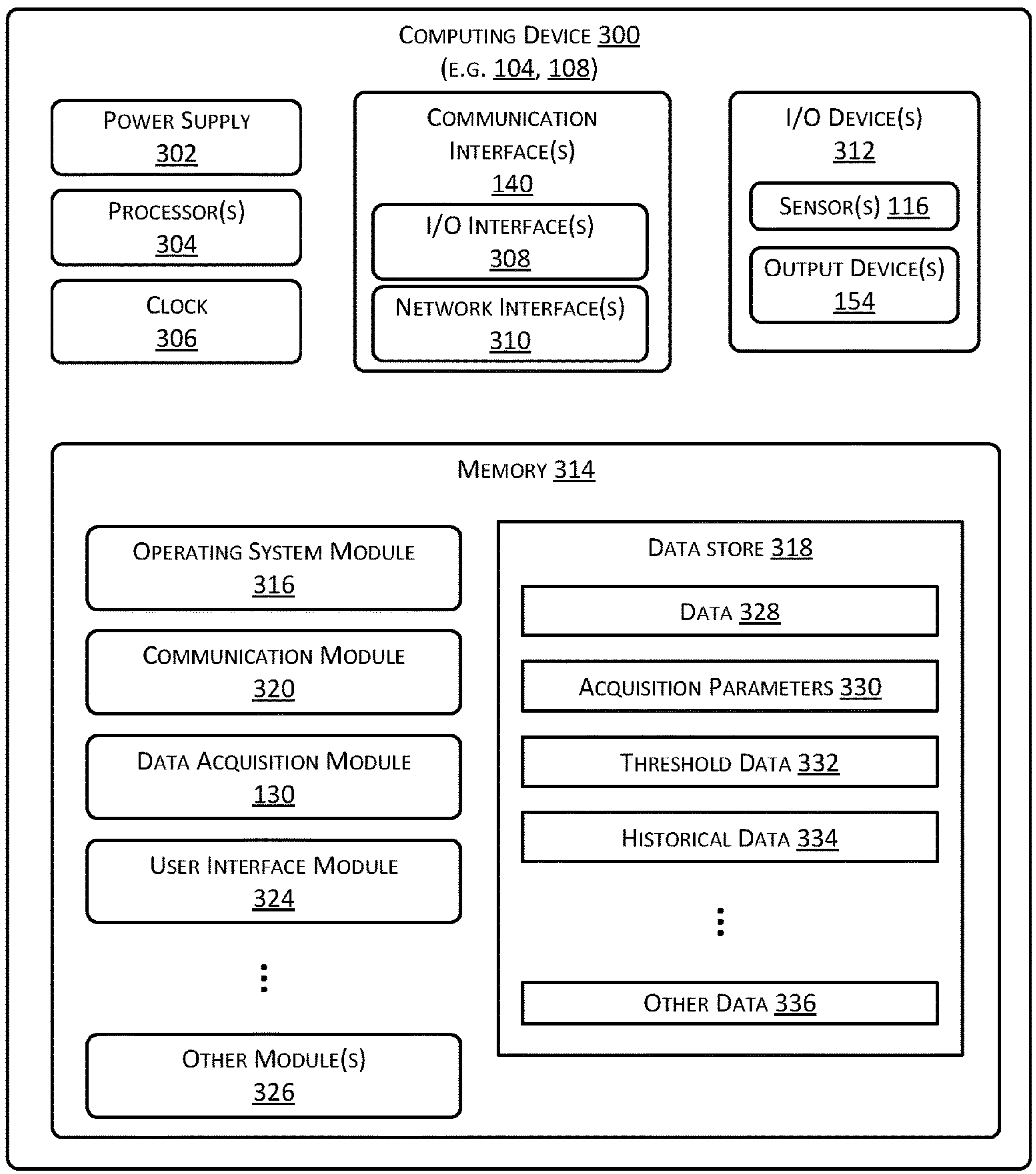
FIG. 3 illustrates a block diagram of a computing device (s) such as a wearable device, smartphone, or other device, according to one implementation.

FIG. 3 illustrates a block diagram of a computing device 300 configured to support operation of the system 100. As described above, the computing device 300 may be the wearable device 104, the computing device 108, a server, other device, or combination thereof.

One or more power supplies 302 are configured to provide electrical power suitable for operating the components in the computing device 300. In some implementations, the power supply 302 may comprise a rechargeable battery, fuel cell, photovoltaic cell, power conditioning circuitry, wireless power receiver, and so forth.

The computing device 300 may include one or more hardware processors 304 (processors) configured to execute one or more stored instructions. The processors 304 may comprise one or more cores. One or more clocks 306 may provide information indicative of date, time, ticks, and so forth. For example, the processor 304 may use data from the clock 306 to generate a timestamp, trigger a preprogrammed action, and so forth.

The computing device 300 may include one or more communication interfaces 140 such as input/output (I/O) interfaces 308, network interfaces 310, and so forth. The communication interfaces 140 enable the computing device 300, or components thereof, to communicate with other devices or components. The communication interfaces 140 may include one or more I/O interfaces 308. The I/O interfaces 308 may comprise interfaces such as Inter-Integrated Circuit (I2C), Serial Peripheral Interface bus (SPI), an inter-integrated circuit sound (I2S) interface, Universal Serial Bus (USB) as promulgated by the USB Implementers Forum, RS-232, and so forth.

The I/O interface(s) 308 may couple to one or more I/O devices 312. The I/O devices 312 may include input devices such as one or more of the sensors 116. The I/O devices 312 may also include output devices 154 such as one or more of an audio output device 154(2), a display device 154(3), and so forth. In some embodiments, the I/O devices 312 may be physically incorporated with the computing device 300 or may be externally placed.

The network interfaces 310 are configured to provide communications between the computing device 300 and other devices, such as the sensors 116, routers, access devices, and so forth. The network interfaces 310 may include devices configured to couple to wired or wireless personal area networks (PANs), local area networks (LANs), wide area networks (WANs), and so forth. For example, the network interfaces 310 may include devices compatible with Ethernet, Wi-Fi, Bluetooth, ZigBee, 4G, 5G, LTE, and so forth.

The computing device 300 may also include one or more busses or other internal communications hardware or software that allow for the transfer of data between the various modules and components of the computing device 300.

As shown in FIG. 3, the computing device 300 includes one or more memories 314. The memory 314 comprises one or more computer-readable storage media (CRSM). The CRSM may be any one or more of an electronic storage medium, a magnetic storage medium, an optical storage medium, a quantum storage medium, a mechanical computer storage medium, and so forth. The memory 314 provides storage of computer-readable instructions, data structures, program modules, and other data for the operation of the computing device 300. A few example functional modules are shown stored in the memory 314, although the same functionality may alternatively be implemented in hardware, firmware, or as a system on a chip (SOC).

The memory 314 may include at least one operating system (OS) module 316. The OS module 316 is configured to manage hardware resource devices such as the I/O interfaces 308, the network interfaces 310, the I/O devices 312, and provide various services to applications or modules executing on the processors 304. The OS module 316 may implement a variant of the FreeBSD operating system as promulgated by the FreeBSD Project; other UNIX or UNIX-like operating system; a variation of the Linux operating system as promulgated by Linus Torvalds; the Windows operating system from Microsoft Corporation of Redmond, Wash., USA; the Android operating system from Google Corporation of Mountain View, Calif., USA; the iOS operating system from Apple Corporation of Cupertino, Calif., USA; or other operating systems.

Also stored in the memory 314 may be a data store 318 and one or more of the following modules. These modules may be executed as foreground applications, background tasks, daemons, and so forth. The data store 318 may use a flat file, database, linked list, tree, executable code, script, or other data structure to store information. In some implementations, the data store 318 or a portion of the data store 318 may be distributed across one or more other devices including the computing devices 300, network attached storage devices, and so forth.

A communication module 320 may be configured to establish communications with one or more of other computing devices 300, the sensors 116, and so forth. The communications may be authenticated, encrypted, and so forth. The communication module 320 may also control the communication interfaces 140.

The memory 314 may also store the data acquisition module 130. The data acquisition module 130 is configured to acquire raw audio data 126, sensor data 124, and so forth. In some implementations the data acquisition module 130 may be configured to operate the one or more sensors 116, the microphone array 118, and so forth. For example, the data acquisition module 130 may determine that the sensor data 124 satisfies a trigger event. The trigger event may comprise values of sensor data 124 for one or more sensors 116 exceeding a threshold value. For example, if a heart rate monitor 116(3) on the wearable device 104 indicates that the pulse of the user 102 has exceeded a threshold value, the microphone array 118 may be operated to generate raw audio data 126.

In another example, the data acquisition module 130 on the wearable device 104 may receive instructions from the computing device 108 to obtain raw audio data 126 at a specified interval, at a scheduled time, and so forth. For example, the computing device 108 may send instructions to acquire raw audio data 126 for 60 seconds every 540 seconds. The raw audio data 126 may then be processed with the first voice activity detector module 134 to determine is speech 122 is present. If speech 122 is detected, the audio data 150 may be obtained and then sent to the computing device 108.

A user interface module 324 provides a user interface using one or more of the I/O devices 312. The user interface module 324 may be used to obtain input from the user 102, present information to the user 102, and so forth. For example, the user interface module 324 may present a graphical user interface on the display device 154(3) and accept user input using the touch sensor 116(4).

One or more other modules 326, such as the data transfer module 138, the turn detection module 156, the speech identification module 158, the audio feature module 164, the feature analysis module 168, the sensor data analysis module 172, the advisory module 176, and so forth may also be stored in the memory 314.

Data 328 may be stored in the data store 318. For example, the data 328 may comprise one or more of raw audio data 126, audio data 150, sensor data 124, user profile data 160, selected audio data 162, sentiment data 170, user status data 174, advisory data 178, output data 152, and so forth.

One or more acquisition parameters 330 may be stored in the memory 314. The acquisition parameters 330 may comprise parameters such as audio sample rate, audio sample frequency, audio frame size, and so forth.

Threshold data 332 may be stored in the memory 314. For example, the threshold data 332 may specify one or more thresholds used by the voice activity detector modules 134 or 146 to determine if the raw audio data 126 includes speech 122.

The computing device 300 may maintain historical data 334. The historical data 334 may be used to provide information about trends or changes over time. For example, the historical data 334 may comprise an indication of sentiment data 170 on an hourly basis for the previous 90 days. In another example, the historical data 334 may comprise user status data 174 for the previous 90 days.

Other data 336 may also be stored in the data store 318.

In different implementations, different computing devices 300 may have different capabilities or capacities. For example, the computing device 108 may have significantly more processor 304 capability and memory 314 capacity compared to the wearable device 104. In one implementation, the wearable device 104 may determine the audio data 150 and send the audio data 150 to the computing device 108. The wearable device 104 may also send other information, such as at least a portion of the sensor data 124 or information based on the sensor data 124, to the computing device 108. In another implementation, the wearable device 104 may generate the sentiment data 170, advisory data 178, and so forth. Other combinations of distribution of data processing and functionality may be used in other implementations.

Figure 4:
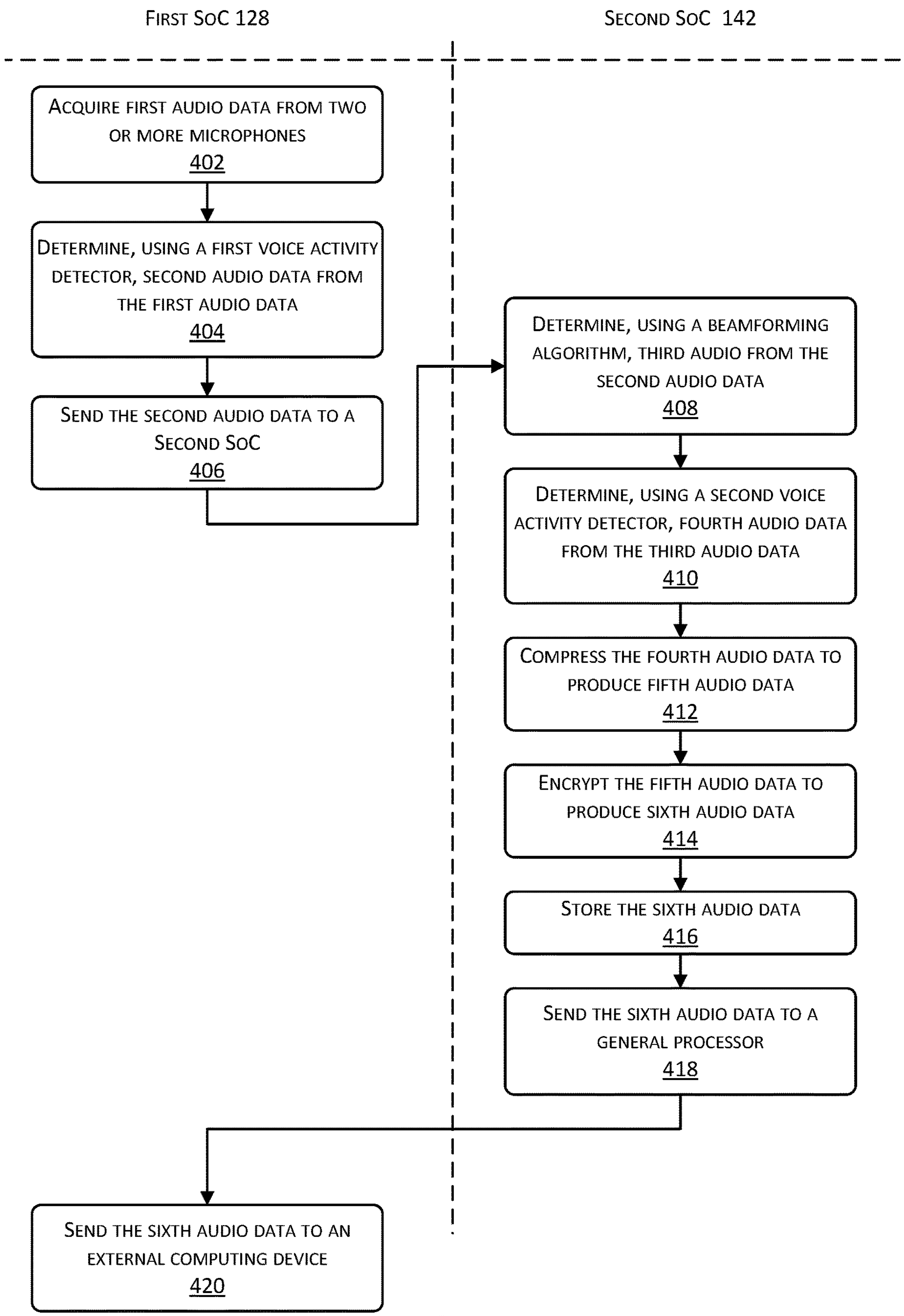
FIG. 4 illustrates a flow diagram of a process performed by the wearable device to generate audio data, according to one implementation.

FIG. 4 illustrates a flow diagram 400 of a process performed by the wearable device 104 to generate audio data 150, according to one implementation. In the implementation depicted, the process is performed using the first SoC 128 and the second SoC 142. In other implementations, other combinations of hardware ranging from a single SoC to various discrete devices may perform the process.

At 402 the first SoC 128 acquires first audio data using the microphone array 118. For example, the codec module 132 may generate the raw audio data 126 from the sounds detected by the first and second microphone 116(5).

At 404 the first SoC 128 determines second audio data using the first voice activity detector 134 to determine a portion of the first audio data that is representative of speech 122.

At 406 the first SoC 128 sends the second audio data to the second SoC 142. For example, the first SoC 128 may store the second audio data in the buffer 136.

In some implementations, responsive to one or more of the determination of the second audio data, the buffer 136 reaching a threshold fill level, or other conditions, the second SoC 142 may be transitioned from an off or low power state to an operational or full power state. For example, to reach the operational state, the second SoC 142 may transition from a first mode to a second mode, wherein the second mode consumes less electrical power than the first mode. In another example, the second SoC 142 may transition from the second mode to the first mode. In some implementations, the transition may include controlling operation of a load switch that provides electrical power to the second SoC 142. The first SoC 128 may receive a signal that the second SoC 142 is ready for use. Once ready, the first SoC 128 may send at least a portion of the second audio data that is stored in the buffer 136 to the second SoC 142. Continuing the example, the second audio data may be sent using an I2S interface.

At 408 the second SoC 142 determines, using a beamforming algorithm, third audio data from the second audio data. For example, the beamforming algorithm may utilize phase information in the second audio data to produce the desired microphone pattern 120. In some implementations the beamforming algorithm may accept as input information about the orientation or positioning of the wearable device 104. For example, the accelerometers 116(10) may provide tilt data that indicates whether the wearable device 104 is flat or vertical. Based at least in part on this information, one or more parameters of the beamforming algorithm may be adjusted to produce a microphone pattern 120 which is expected to include the head of the user 102. The speech 122 that may be present in the third audio data may exhibit a greater signal to noise ratio (SNR) as a result of the beamforming, due to the effective gain towards the head of the user 102 and the attenuation in noise outside the microphone pattern 120.

At 410 the second SoC 142 determines, using the second voice activity detector module 146, fourth audio data that is representative of speech 122 in at least a portion of the third audio data. The second voice activity detector module 146 operates to increase the likelihood that the audio data processed to determine the sentiment data 170 actually includes speech 122. In one implementation, the first voice activity detector module 134 uses a first voice detection algorithm with a first set of one or more threshold values, while the second voice activity detector module 146 uses a second voice detection algorithm with a second set of one or more threshold values. In another implementation, the first voice activity detector module 134 and the second voice activity detector module 146 may use the same algorithm, but with different threshold values.

At 412 the second SoC 142 compresses the fourth audio data to produce fifth audio data. For example, the audio compression and encryption module 148 may implement the Opus audio compression as promulgated by opus-codec.org.

At 414 the second SoC 142 encrypts the fifth audio data to produce sixth audio data. For example, the second SoC 142 may use a public key associated with the computing device to encrypt the fifth audio data.

At 416 the sixth audio data is stored. In some implementation the sixth audio data may be stored for further processing, until there is an opportunity to send to the computing device 108, and so forth.

At 418 the second SoC 142 sends the sixth audio data to the first SoC 128. For example, the second SoC 142 may send the sixth audio data to the first SoC 128 using SPI.

At 420, the first SoC 128 may receive the sixth audio data and send that sixth audio data to an external computing device. For example, the first SoC 128 may use a Bluetooth wireless communication interface to send the sixth audio data to the computing device 108. In some implementations the sixth audio data may be encrypted during transmission. For example, the Bluetooth communication link may be encrypted, and the data sent via the Bluetooth communication link may be encrypted.

In another implementation (not shown) the first SoC 128, the second SoC 142, or another component in the wearable device 104 may perform one or more of the functions associated with turn detection, speech identification, and so forth. For example, the second SoC 142 may be used to determine the sentiment data 170.

Figure 5:
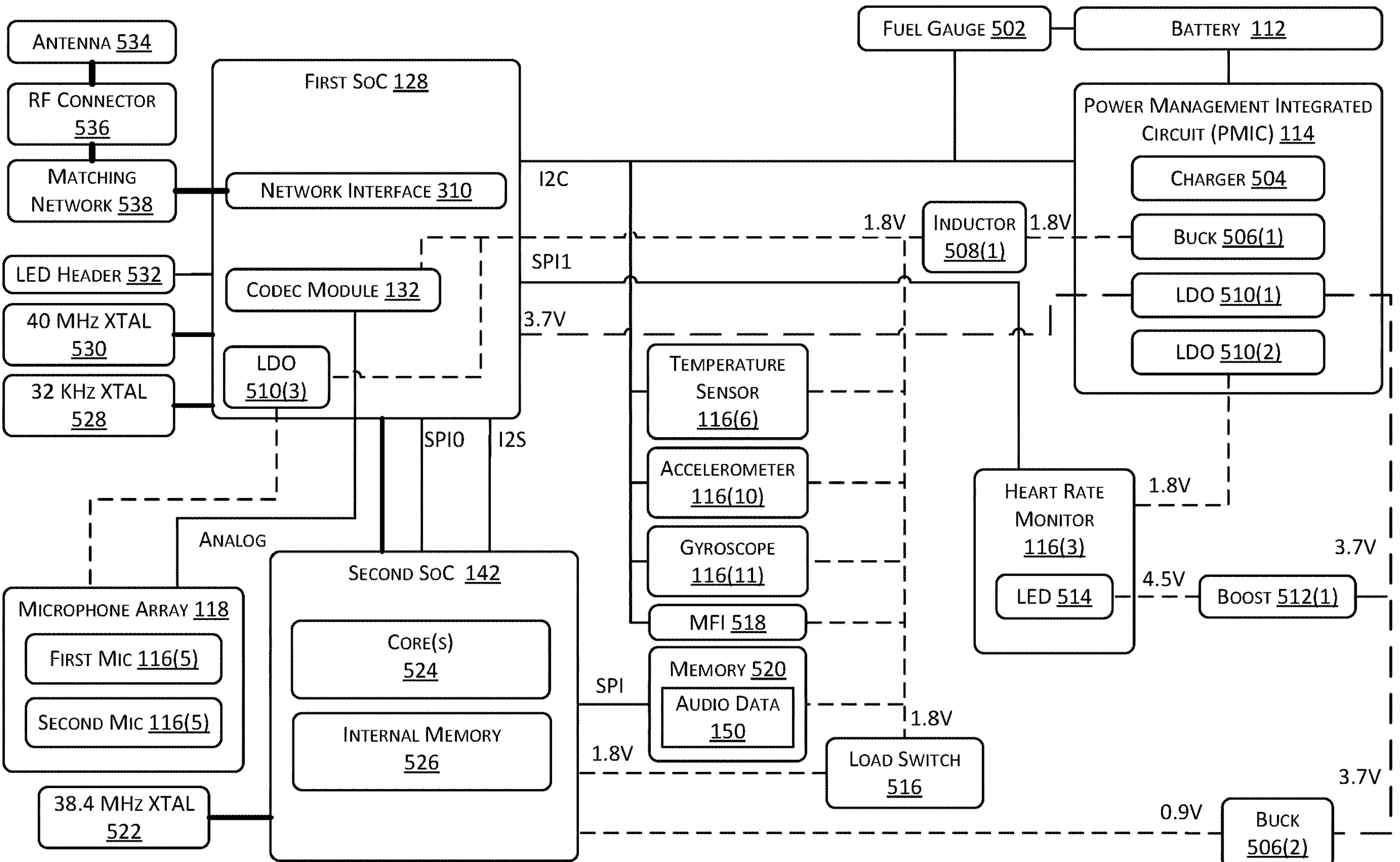
FIG. 5 is a block diagram of the wearable device, according to one implementation.

FIG. 5 is a block diagram 500 of the wearable device 104, according to one implementation. To improve clarity of this figure, some components, modules, lines, and other features have been omitted. For example, the cores, memory, busses, and so forth in the SoCs are not necessarily shown.

The battery 112 is connected to a fuel gauge 502. The fuel gauge 502 is also in communication with the first SoC 128. For example, the fuel gauge 502 may be connected to the first SoC 128 via I2C. The fuel gauge 502 may provide data such as current state or charge of the battery 112, battery health, battery temperature, and so forth. The battery 112 may comprise one or more rechargeable cells. For example, the battery 112 may comprise a lithium ion battery with a nominal 3.8 V output voltage.

The PMIC 114 includes circuitry for power management. For example, the PMIC 114 may comprise a TI BQ25120A from Texas Instruments Inc. of Dallas, Tex., United States of America. The PMIC 114 is in communication with the first SoC 128. For example, the PMIC 114 may be connected to the first SoC 128 via I2C. The PMIC 114 may include a charger 504 that controls charging the battery 112 using an external power source.

The PMIC 114 may include one or more step-down converters (bucks) 506. The buck 506 reduces or steps down a supply voltage to a lower load voltage. For example, a buck 506 may accept as input the battery voltage of 3.8 V and produce as output 1.8 V.

One or more inductors 508 may be present. For example, as shown here an inductor 508(1) that is external to the PMIC 114 may be connected to the output of a buck 506(1) that produces an output voltage of 1.8 V. The inductor 508(1) in turn may be connected to the codec module 132 in the first SoC 128, various sensors 116 such as the temperature sensor 116(6), accelerometer 116(10), gyroscope 116(11), "Made for iPhone" (MFI) 518 device, a load switch 516, and so forth. The various sensors 116, the MFI 518 device, and the load switch 516 are in communication with the first SoC 128. For example, the temperature sensor 116(6), accelerometer 116(10), gyroscope 116(11), the load switch 516, the MFI 518 device, and so forth may be connected to the first SoC 128 via I2C.

The PMIC 114 may include one or more low dropout regulators (LDO) 510 that provide regulated output voltage. For example, a first LDO 510(1) may provide a regulated 3.7 V to the first SoC 128, a buck 506(2), and a boost 512(1).

The buck 506(2) may step down the regulated 3.7 V to 0.9 V which is then provided to the second SoC 142.

A step-up converter (boost) 512 increases or steps up a supply voltage to a higher load voltage. In this illustration, the boost 512(1) raises the 3.7 V provided by the LDO 510(1) to 4.5 V. This 4.5 V is provided to driver circuitry to operate one or more light emitting diodes (LEDs) 514 in the heart rate monitor 116(3). By using the arrangement of LDO 510(1) and boost 512(1), voltage ripple is minimized. By minimizing voltage ripple, the optical SNR of the heart rate monitor 116(3) is improved.

A second LDO 510(2) may provide a regulated 1.8 V to the heart rate monitor 116(3). The heart rate monitor 116(3) is in communication with the first SoC 128. For example, the heart rate monitor 116(3) may be connected to the first SoC 128 via SP11.

The load switch 516 is used to control the 1.8 V power supplied to the second SoC 142 by the first buck 506(1). For example, when the second SoC 142 is not in use, the load switch 516 may be set to prevent the flow of current to the second SoC 142. In one implementation if an elapsed time has passed since the second SoC 142 has been used to determine or otherwise process audio data or a portion thereof, the load switch 516 may operate to discontinue providing electrical power to the second SoC 142. In other implementations other load switches 516 may be present. For example, a second load switch may be used to control the 0.9 V power supplied to the second SoC 142 by the first LDO 510(1). The load switch 516 may comprise a field effect transistor, relay, transistor, or other device.

The MFI 518 device provides various functionality that is associated with interoperation, communication, and other functionality for products compliant with the specification promulgated by Apple Corporation of Cupertino, Calif., United States of America. For example, the MFI 518 device may be used to establish, maintain, and otherwise support Bluetooth communications with other devices, including those produced by Apple Corp.

The second SoC 142 may be connected via SPI to memory 520. The memory 520 may comprise non-volatile flash random access memory (RAM). For example, the memory 520 may comprise W25Q128FV16 MB memory from Winbond from Winbond Electronics Corporation of Taiwan. During operation the memory 520 may be used to store the audio data 150 that is produced by the second SoC 142. In some implementations the memory 520 may also store one or more of the sensor data 124, the user status data 174, and so forth. The memory 520 may be powered by the 1.8 V provided by the first buck 506(1).

A 38.4 MHz crystal 522 may provide timing for the second SoC 142. In some implementations the crystal 522 may be internal to the second SoC 142.

The second SoC 142 may include one or more cores 524 and internal memory 526. The number of cores 524 and the internal memory 526 that is enabled and operational may be configurable. For example, the second SoC 142 may have two cores 524(1) and 524(2) with 4 MB of embedded SRAM as the internal memory 526. If the expected computational load to perform the various functions can be performed by a single core 524, in one implementation the first core 524(1) may be used while the second core 524(2) is turned off. Likewise, if the memory footprint during operation is expected to be less than 2 MB, the unused 2 MB of the internal memory 526 may be turned off. By turning off these unused components, the power consumption during operation is further reduced, extending the operational runtime.

The first SoC 128 may include an integrated third LDO 510(3). The third LDO 510(3) may be supplied by the 1.8V from the inductor 508(1) and the first buck 506(1). The third LDO 510(3) provides a biasing voltage to the first microphone 116(5) and the second microphone 116(5) of the microphone array 118. Each of the microphones 116(5) provide an analog signal to the codec module 132. As described above, the codec module 132 may use an analog to digital converter to generate a digital representation of the analog input.

The first SoC 128 may have timing provided by one or more of a 32 KHz crystal 528 or a 40 MHz crystal 530. In some implementations the crystals 528 or 530 may be internal to the first SoC 142.

By having separate crystals for the first Soc 128 and the second SoC 142, the overall design of the wearable device 104 is simplified. This also allows the second SoC 142 to be turned off or transitioned to a low power mode when not in use, while leaving the first SoC 128 operational. The first SoC 128 may generate the clock signal used for the I2S interface to the second SoC 142. For example, the first SoC 128 may provide a 1.024 MHz BCLK signal for the I2S interface to the second SoC 142. The first SoC 128 may be the I2S bus master.

An LED header 532 may be connected to the first SoC 128. One or more LEDs used to provide output to the user 102 may be connected to the LED header 532.

The network interface 310 may comprise a wireless communication interface. For example, the network interface 310 may comprise a transceiver that is compliant with the Bluetooth wireless communication specifications and is compatible with Bluetooth protocols.

An antenna 534 may be connected to a radio frequency (RF) connector 536 which in turn is connected to a matching network 538. The matching network 538 may then be connected to the transceiver. For example, the antenna 534 may comprise one or more electrically conductive elements arranged proximate to a top surface of the wearable device 104. The matching network 538 may comprise one or more of inductors, capacitors, tuned circuits, and so forth to provide an impedance match between the transceiver and the antenna 534.

Figure 6:
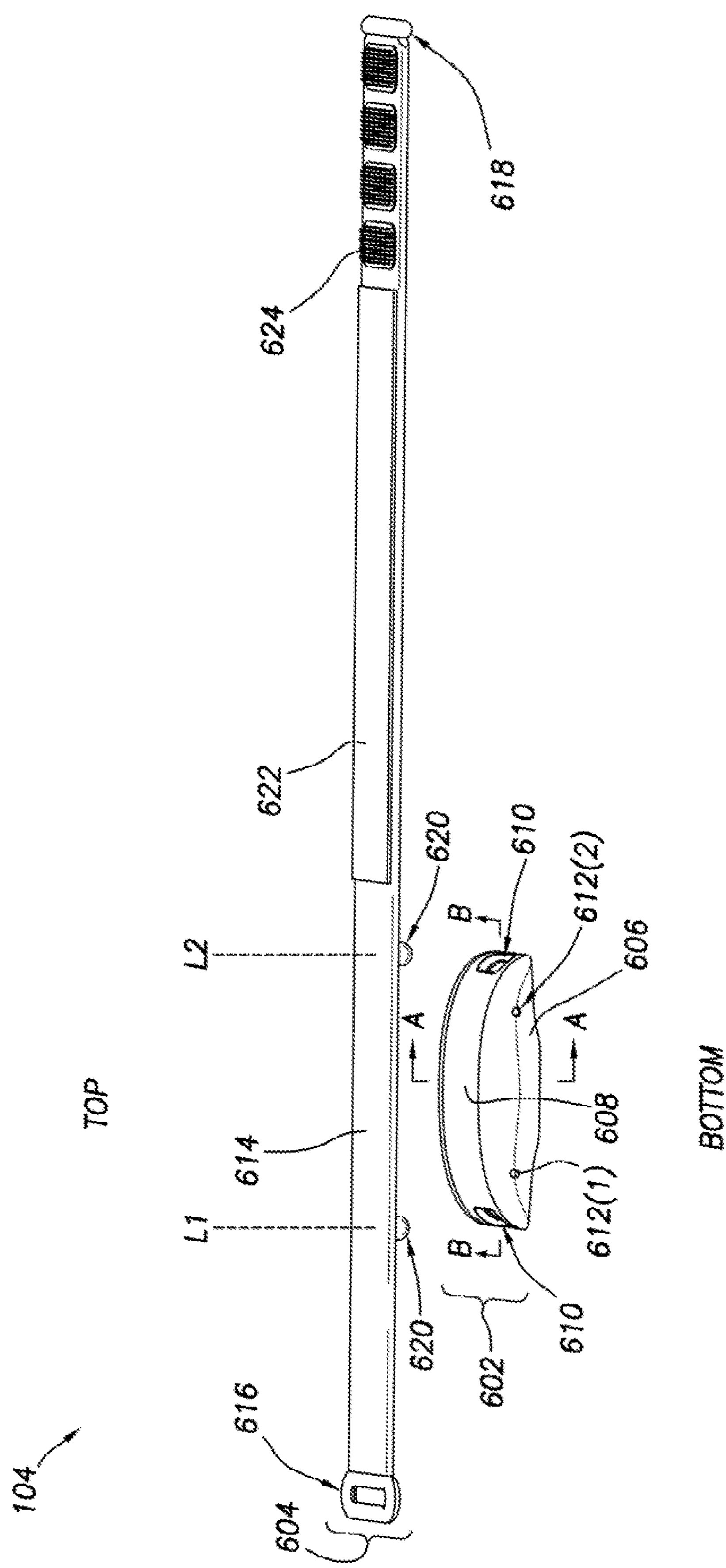
FIG. 6 is an illustrative wearable device, according to one implementation.

FIG. 6 is an illustrative view of a wearable device 104, according to one implementation. The wearable device 104 comprises a housing 602 and a band 604. The housing 602 may comprise a body 606 and an upper cover 608. The body 606, upper cover 608, and other components may comprise one or more of a metal, plastic, composite, ceramic, and so forth.

The body 606 may include one or more openings. For example, during assembly components may be placed within the body 606 through an opening that is then closed by the upper cover 608. The body 606 and the upper cover 608 may be joined such that the resulting housing 602 is sealed. In the implementation shown here, an upper surface of the housing 602 is curved. During wear, the upper surface of the housing 602 faces away from the portion of the user 102 to which the wearable device 104 is retained. A lower surface of the housing 602 is proximate to the portion of the user 102. For example, at least a portion of the lower surface may be in contact with the user 102 while the wearable device 104 is being worn.

The body 606 includes one or more receptacles 610. As illustrated here, the body 606 is generally rectangular when viewed from above, with two ends. In the implementation depicted here a first receptacle 610 is proximate to a first end of the body 606 while a second receptacle 610 is proximate to a second end of the body 606. Each receptacle 610 has an opening on the upper surface of the housing 602. For example, the receptacle 610 may be within the body 606 while the upper cover 608 includes apertures for each of the openings of the receptacles 610.

Each receptacle 610 is configured such that the opening or entry to the receptacle 610 is smaller along at least one dimension than an interior volume of the receptacle 610. For example, each receptacle 610 may include a retention ridge that is proximate to the opening in the receptacle 610. The retention ridge introduces a constriction or narrowing. For example, in cross-section the receptacle 610 may appear to resemble a mushroom shape with a root or stalk that is narrower than a larger, bulbous tip. In some implementations the retention ridge may extend along the entire perimeter of the opening.

The housing 602 may include one or more apertures 612. The body 606 may include several apertures 612 for microphone ports, light emitting diodes, air pressure sensors, and so forth. In this view, apertures 612(1) and 612(2) are shown on a first side of the housing 602. For example, the aperture 612(1) may comprise a pressure equalization port and the aperture 612(2) may provide a port for a first microphone 116(5) to receive sound from outside the housing 602.

The band 604 may comprise a flexible member 614 having a first end and a second end. The flexible member 614 includes an inner surface and an outer surface. When the band 604 is affixed to the housing 602, at least a part of the inner surface of the flexible member 614 is proximate to the upper surface of the housing 602.

The flexible member 614 may comprise one or more of fabric, an elastomeric material, a plurality of links, and so forth. For example, the flexible member 614 may comprise an elastic fabric. A loop 616 may be arranged at the first end of the flexible member 614 while an endcap 618 is arranged at the second end. The loop 616 may be a rigid loop. For example, the loop 616 may comprise metal that is encased in plastic. In other implementations, the loop 616 may comprise a flexible material.

One or more protrusions 620 extend away from the inner surface of the flexible member 614. In the implementation shown here, a first protrusion 620 extends from the inner surface of the flexible member 614 at a first location L1 and a second protrusion 620 extends from the inner surface at a second location L2.

Each protrusion 620 is configured to maintain mechanical engagement after insertion into the receptacle 610. The protrusions 620 may comprise an elastomeric material. In one implementation, the protrusions 620 may comprise silicone rubber having a hardness as measured using a durometer with a Shore A reading of between 70 and 90.

In one implementation, the protrusions 620 may comprise components that have been joined to the flexible member 614. For example, the protrusions 620 may be formed and then joined to the flexible member 614 using one or more of an adhesive, mechanical fasteners, thread, and so forth.

In another implementation the protrusions 620 may be integral with at least a portion of the flexible member 614. For example, the flexible member 614 and the protrusions 620 may comprise a unitary piece of elastomeric material.

A portion of each protrusion 620 is larger than the narrowest part of the opening into the receptacle 610. For example, a first distance D1 indicates the maximum width of the opening in the receptacle 610. A second distance D2 indicates the maximum interior width of interior space of the receptacle 610 at the widest point. Due to the constriction in the receptacle 610, the first distance D1 is less than the second distance D2.

A third distance indicates the maximum width of the protrusion 620 at its widest point. The third distance is greater than the first distance D1. For example, at the widest point the bulbous tip of the protrusion 620 is larger than the opening of the receptacle 610. In one implementation, the third distance of the maximum width of the protrusion 620 may be at least 15% greater than the first distance D1.

In one implementation the third distance may be less than the second distance D2. For example, the widest point of the protrusion 620 may be smaller than the largest width of the receptacle 610. In another implementation the uncompressed protrusion 620 may have a third distance that is greater than the second distance D2. For example, after insertion into the receptacle 610 the protrusion 620 may expand and exert some pressure on the interior surface of the receptacle 610 as the elastomeric material attempts to resume a prior shape. In this implementation the portion of the protrusion 620 that is within the receptacle 610 remains at least slightly compressed.

In the implementation depicted here, each of the two protrusions 620 extending from the inner surface of the flexible member 614 has a corresponding receptacle 610. The band 604 is affixed to the housing 602 by placing the inner surface of the flexible member 614 in contact with the outer surface of the upper cover 608, placing the band 604 atop the housing 602. For example, the inner surface of the flexible member 614 between L1 and L2 may be in contact with the upper cover 608.

Each protrusion 620 is aligned to a respective receptacle 610 and a force is applied to the flexible member 614 on the outer surface opposite the protrusion 620. The applied force causes the enlarged portion of the protrusion 110 to temporarily deform, allowing it to pass into the cavity of the receptacle 610. In some implementations an audible "pop" or other sound is produced, providing audible feedback to the user 102 that the band 604 and the housing 602 have been adequately engaged. Once within the receptacle 610, the elastomeric material expands, securing part of the protrusion 620 within the receptacle 610. The band 604 is now affixed to the housing 602.

To separate the band 604 from the housing 602, the process is reversed. A pull may be applied to the flexible member 614. Under the influence of the pull, the protrusion 620 temporarily deforms and is able to be withdrawn from the receptacle 610. In some implementations an audible "pop" or other sound is produced, providing audible feedback to the user 102 that the band 604 and the housing 602 have been separated.

In one implementation, the one or more receptacles 610 in the housing 602 may be configured with the same dimensions. Likewise, the one or more protrusions 620 on the band 604 may be configured with the same dimensions. In this implementation, the relative orientation of the housing 602 with respect to the band 604 may be easily changed. For example, a left-handed user 102 may wish to reverse the orientation of the housing 602 with respect to the band 604 to allow improved access to one or more controls on the housing 602. In other implementations the dimensions of one or more of the receptacles 610 or the protrusions 620 may differ, enforcing a particular orientation of the band 604 with respect to the housing 602.

Instead of an elastomeric material, the protrusions 620 may comprise one or more spring elements. For example, the protrusions 620 may comprise a metal or plastic element that forms a living hinge. In another example, the protrusions 620 may comprise one or more features that are biased using one or more compression springs.

With the housing 602 and the band 604 attached, the wearable device 104 may be worn by a user 102. The flexible member 614 may include on the outer surface a loop portion 622 comprising a plurality of loops and a hook portion 624 comprising a plurality of hooks. To affix the wearable device 104 to the user 102, the second end of the flexible member 614 having the endcap 618 is passed through the loop 616. The user 102 may place their forearm into the loop formed by the flexible member 614. The second end of the flexible member 614 may then be pulled such that the inner surface is in comfortable contact with the user 102's forearm, and the hook portion 624 is then pressed against the loop portion 622, securing the flexible member 614.

In other implementations, other mechanisms may be used to secure the wearable device 104 to the user 102. For example, the flexible member 614 may utilize a buckle, a folding clasp, butterfly closure, and so forth. In another example, the flexible member 614 may comprise a contiguous loop of elastomeric material, allowing the user 102 to pass their hand through the loop and which then contracts to hold the wearable device 104 in place.

At least a portion of the flexible member 614 between the first location L1 and the second location L2 may comprise an elastomeric material. A distance between the receptacles 610 may be slightly greater than the distance between L1 and L2. In this implementation, during and after installation the portion of the band 604 between L1 and L2 is under tension from the elastomeric material of the flexible member 614 attempting to resume a prior shape. This tension provides a biasing force that assists in keeping the inner surface of the flexible member 614 in contact with the upper surface of the housing 602. By maintaining contact, the flexible member 614 is not wrinkled or otherwise protruding, thus preventing snags, preventing contaminants from accumulating in between the two, and improving the aesthetics of the wearable device 104.

In some implementations the housing 602 may include one or more output devices on the upper surface. For example, a display device may be arranged on the upper surface between the receptacles 610 to provide visual output to the user 102. At least a portion of the flexible member 614 that is between the first location L1 and the second location L2 may be transparent, contain one or more holes, or another opening to allow at least a portion of the display device to be visible. For example, the flexible member 614 may comprise a transparent material such as silicone rubber. In another example, the flexible member 614 may comprise an opening or aperture that is coincident with the display device. In another example, the flexible member 614 may comprise a plurality of holes, perforations, or spaces between threads that allow at least a portion of light from the display device to pass through.

Figure 7:
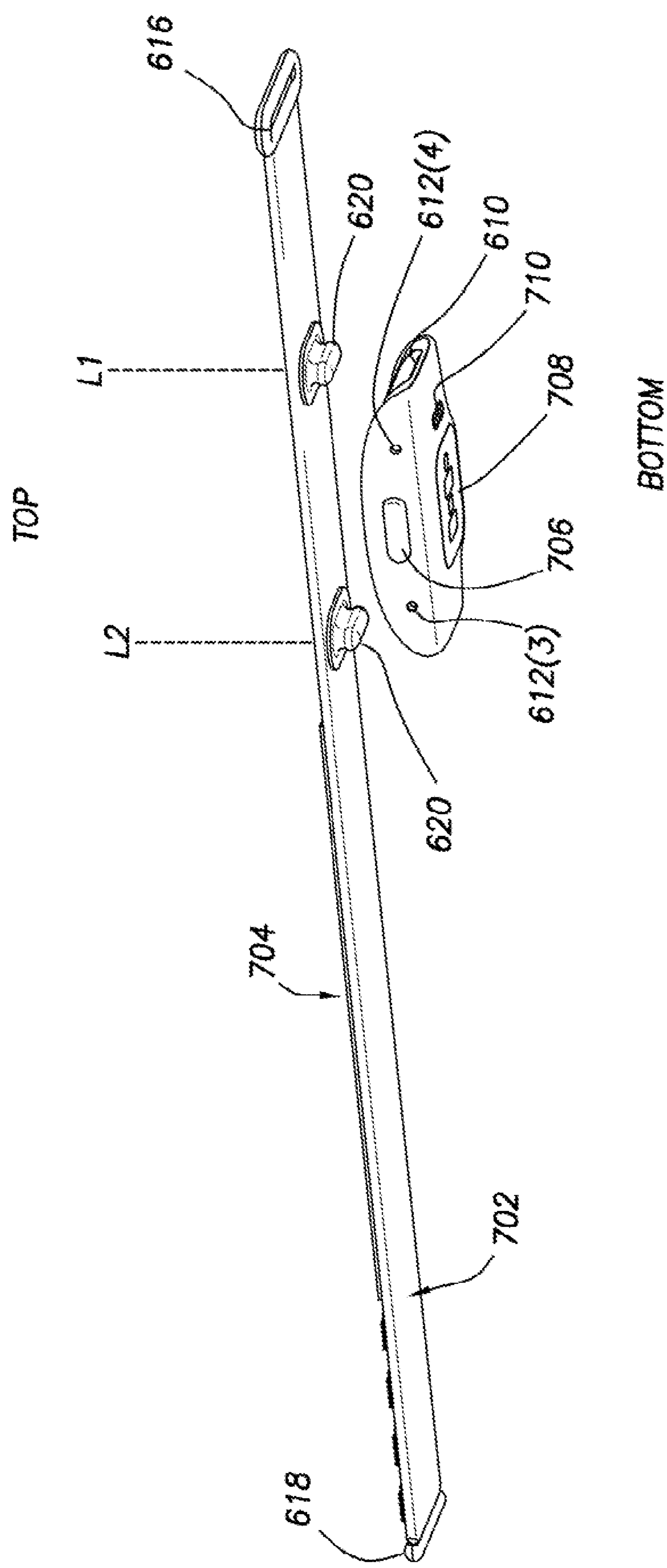
FIG. 7 is another view of the wearable device of FIG. 6, according to one implementation.

FIG. 7 is another view of the wearable device 104 of FIG. 6 with the band 604 not yet affixed to the housing 602, according to one implementation. In this view, the inner surface 702 and the outer surface 704 of the flexible member 614 are shown. In this view additional apertures 612(3) and 612(4) are shown. For example, the aperture 612(3) may provide a path for light from an LED to exit the housing 602 while the aperture 612(4) may provide a port for a second microphone 116(5) to receive sound from outside the housing 602.

A button 706 is also present on this side of the housing 602 between the apertures 612(3) and 612(4). The button 706 may be used to activate a switch to allow for user 102 input.

A sensor window 708 is arranged on a bottom surface of the housing 602. The sensor window 708 may be transparent to one or more wavelengths of light. For example, the sensor window 708 may be transparent to visible and infrared light. The sensor window 708 may be used by one or more sensors to obtain information about the user 102. A field of view of one or more sensors may pass through the sensor window 708. For example, an optical heart rate monitor 116(3) may comprise an LED that emits light which passes through the sensor window 708 and to the arm of the user 102. Reflected or scattered light returns through the sensor window 708 where it is measured by a photodetector. In another example a camera may have a field of view that passes through the sensor window 708 to obtain images of a portion of the user 102's arm.

In some implementations, the portion of the bottom surface of the housing 602 that includes the sensor window 708 may protrude away from the remainder of the bottom surface.

One or more electrical contacts 710 may also be present on the bottom surface of the housing 602. The electrical contacts 710 may be used to transfer data, provide electrical power, and so forth. In some implementations the electrical contacts 710 may be recessed with respect to the bottom surface.

Figure 8:
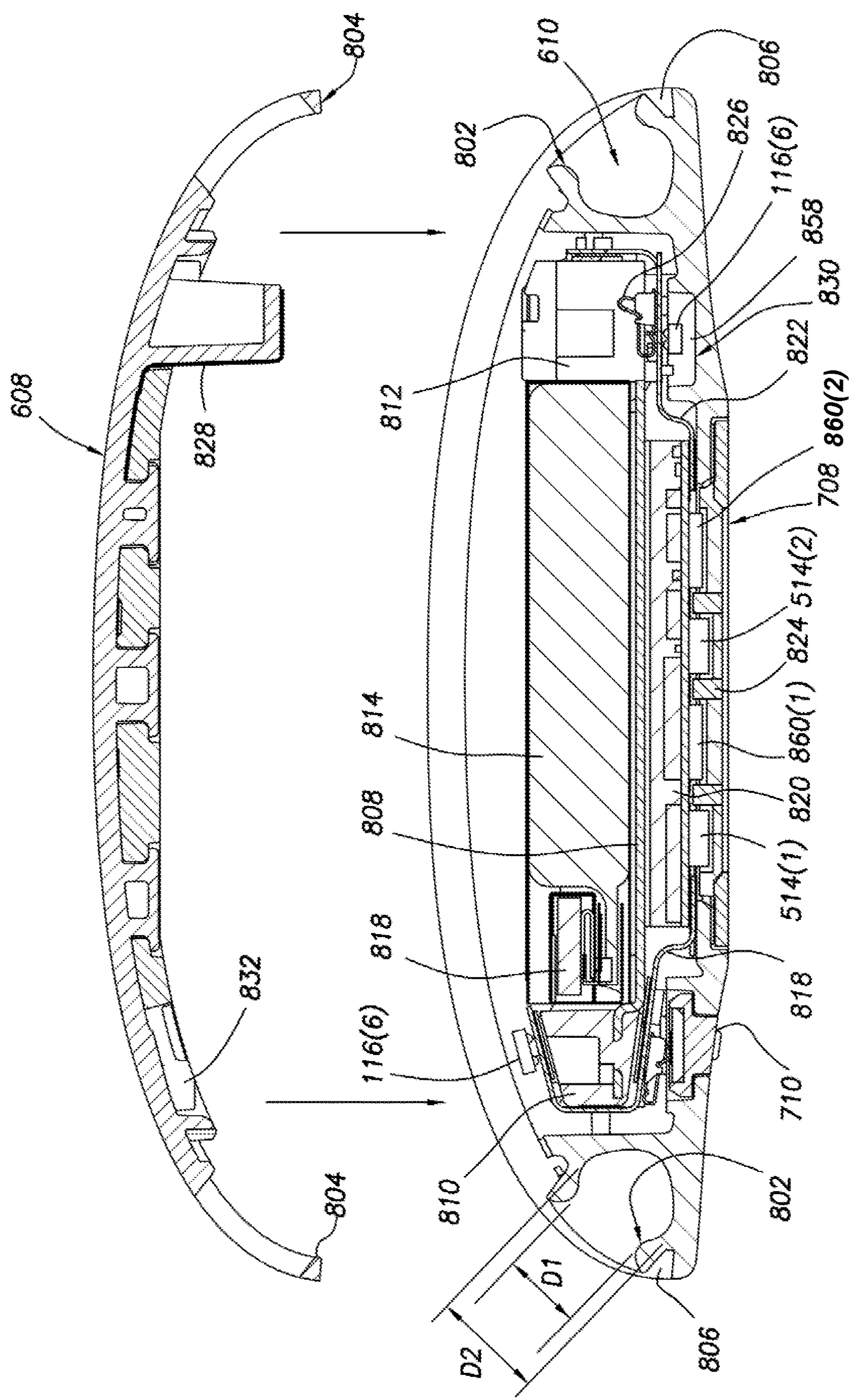
FIG. 8 is a cross sectional view of the housing, according to one implementation.

FIG. 8 is a cross sectional view of the housing 602 along line B-B (as shown in FIG. 6), according to one implementation. In this view the upper cover 608 is shown separate from the housing 602.

The receptacles 610 are visible here. Each receptacle 610 has a retention ridge 802 proximate to the entry of the receptacle 610. In another implementation other engagement features may be used. For example, teeth may extend from the housing 602. The opening of the receptacle 610, the retention ridge 802, and the interior cavity of the receptacle 610 may be rounded or otherwise avoid sharp edges. Rounding of these features may facilitate controlled installation and removal of the protrusion 620 and may also improve lifespan of the protrusion 620 by preventing tearing.

The first distance D1 indicates the maximum width of the opening in the receptacle 610, as constrained by the retention ridge 802 or other feature. The second distance D2 indicates the maximum interior width of the receptacle 610 at the widest point of the interior space within the receptacle 610. Due to the constriction in the receptacle 610, the first distance D1 is less than the second distance D2.

The upper cover 608 may include a first lip 804 and a second lip 804. The first lip 804 may be proximate to a first end of the upper cover 608 while the second lip 804 may be proximate to a second end of the upper cover 608. The first lip 804 and the second lip 804 extend from an inside surface of the upper cover 608. For example, in cross section of the upper cover 608 may resemble a "C".

The housing 602 may also include one or more recesses 806. For example, the housing 602 may include a first recess 806 that is proximate to the first end the housing 602 and a second recess 806 that is proximate to the second end of the housing 602. The recess 806 is configured to accept the corresponding lip 804 and retain the upper cover 608 to the housing 602. For example, during assembly, an adhesive is placed within a groove and the upper cover 608 is moved into contact with the housing 602. Upon application of a force bringing the upper cover 608 and the housing 602 together, a ridge enters the groove and the first lip 804 enters the first recess 806 and the second lip 804 enters the second recess 806.

A metal chassis 808 is also shown. Various components may be mounted to the metal chassis 808. A first end of the metal chassis 810 and a second end of the metal chassis 812 may include features to facilitate mounting of other components. For example, the metal chassis 808 may include holes that permit the passage of a mechanical fastener such as a screw.

The battery 112 may be placed within the housing 602. A battery contact block provides electrical connections between contacts on the battery 112 and the electronics of the wearable device 104. A flexible printed circuit (FPC) 818 provides one or more electrical traces to transfer one or more of power or data between components of the wearable device 104.

The wearable device 104 may utilize a system in package (SIP) construction, as shown with a SIP 820. The SIP 820 may comprise the first SoC 128, the second SoC 142, the memory 520, the PMIC 114, or other components. The FPC 818 or other FPCs, wiring harnesses, and so forth may be used to interconnect the components in the wearable device 104.

A FPC 822 may be used as a transmission line to transfer radio frequency signals between the SIP 820 and one or more antenna contacts 826. When the upper cover 608 is installed on the housing 602 the antenna contacts 826 provide an electrical connection between the FPC 822 and a portion of an antenna trace 828. The antenna trace 828 may extend along a portion of an inner surface of the upper cover 608. The antenna trace 828 may be used as the antenna 534.

Also shown in this view is a window barrier 824 that is located between the sensor window 708 and the interior of the housing 602. For example, the heart rate monitor 116(3) may include a multicolor LED 514(1), a first photodiode 860(1), a green LED 514(2), and a second photodiode 860(2). The LEDs 514 are operated to emit light and one or more of the photodiodes 860 or other photodetectors detect the light reflected or scattered by the arm of the user 102. The window barrier 824 may provide an opaque barrier between the LED and the photodetector to prevent the emitted light from intruding on and saturating the photodetector. The window barrier 824 also provides mechanical support to the sensor window 708.

Also shown are the contacts 710 on an underside of the housing 602.

A first temperature sensor 116(6) may be positioned proximate to the bottom surface of the housing 602. The first temperature sensor 116(6) may be used to determine the temperature of the user 102. In this illustration the first temperature sensor 116(6) may be arranged at least partially within a well or recess 830 in the housing 602 that is proximate to the bottom surface. A thermally conductive gel, grease, or other material may be arranged around or between the first temperature sensor 116(6) and the walls of the well 830. The housing 602, or a bottom portion thereof, may comprise a thermally conductive material such as stainless steel.

A second temperature sensor 116(6) may be positioned proximate to a top surface of the wearable device 104. For example, the second temperature sensor 116(6) may be proximate to the inner surface of the upper cover 608.

Specific physical embodiments as described in this disclosure are provided by way of illustration and not necessarily as a limitation. Those having ordinary skill in the art readily recognize that alternative implementations, variations, and so forth may also be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features, structures, and acts are disclosed as exemplary forms of implementing the claims.

Processes discussed herein may be implemented in hardware, software, or a combination thereof. In the context of software, the described operations represent computer-executable instructions stored on one or more non-transitory computer-readable storage media that, when executed by one or more processors, perform the recited operations. Generally, computer-executable instructions include routines, programs, objects, components, data structures, and the like that perform particular functions or implement particular abstract data types. Those having ordinary skill in the art will readily recognize that certain steps or operations illustrated in the figures above may be eliminated, combined, or performed in an alternate order. Any steps or operations may be performed serially or in parallel. Furthermore, the order in which the operations are described is not intended to be construed as a limitation.

Embodiments may be provided as a software program or computer program product including a non-transitory computer-readable storage medium having stored thereon instructions (in compressed or uncompressed form) that may be used to program a computer (or other electronic device) to perform processes or methods described herein. The computer-readable storage medium may be one or more of an electronic storage medium, a magnetic storage medium, an optical storage medium, a quantum storage medium, and so forth. For example, the computer-readable storage media may include, but is not limited to, hard drives, optical disks, read-only memories (ROMs), random access memories (RAMs), erasable programmable ROMs (EPROMs), electrically erasable programmable ROMs (EEPROMs), flash memory, magnetic or optical cards, solid-state memory devices, or other types of physical media suitable for storing electronic instructions. Further, embodiments may also be provided as a computer program product including a transitory machine-readable signal (in compressed or uncompressed form). Examples of transitory machine-readable signals, whether modulated using a carrier or unmodulated, include, but are not limited to, signals that a computer system or machine hosting or running a computer program can be configured to access, including signals transferred by one or more networks. For example, the transitory machine-readable signal may comprise transmission of software by the Internet.

Separate instances of these programs can be executed on or distributed across any number of separate computer systems. Thus, although certain steps have been described as being performed by certain devices, software programs, processes, or entities, this need not be the case, and a variety of alternative implementations will be understood by those having ordinary skill in the art.

Additionally, those having ordinary skill in the art will readily recognize that the techniques described above can be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features and acts are disclosed as illustrative forms of implementing the claims.

What is claimed is:

1. A wearable device comprising:
at least one microphone;
a heart rate monitor;
a first system on a chip (SoC) comprising:
a first wireless communication interface;
a first memory storing first computer-executable instructions; and
a first hardware processor that executes the first computer-executable instructions to:
determine sensor data using the heart rate monitor;
determine that one or more values in the sensor data exceed a first threshold value;
responsive to the one or more values in the sensor data exceeding the first threshold value, acquire first audio data using the at least one microphone;
determine second audio data using a first voice activity detector to determine a portion of the first audio data that is representative of speech; and
send the second audio data to a second SoC; and
the second SoC comprising:
a second memory storing second computer-executable instructions; and
a second hardware processor that executes the second computer-executable instructions to:
receive the second audio data;
determine third audio data using a second voice activity detector to determine a portion of the second audio data that is representative of speech; and
compress the third audio data to produce fourth audio data.

2. The wearable device of claim 1, wherein:
the first voice activity detector uses a second threshold value to determine speech,
the second voice activity detector uses a third threshold value to determine speech, and
the second threshold value is less than the third threshold value.

3. The wearable device of claim 1, wherein:
the first voice activity detector uses a first voice detection algorithm with a first set of one or more threshold values, and
the second voice activity detector uses a second voice detection algorithm with a second set of one or more threshold values.

4. The wearable device of claim 1, wherein the second computer-executable instructions to determine the third audio data using the second voice activity detector comprise second computer-executable instructions to:
determine, using a beamforming algorithm, fifth audio data from the second audio data; and
determine the portion of the second audio data based on the fifth audio data.

5. The wearable device of claim 1, further comprising:
the second hardware processor executes the second computer-executable instructions to:
encrypt the fourth audio data to produce fifth audio data;
store the fifth audio data;
receive, from the first SoC, an instruction to send the fifth audio data; and
send the fifth audio data to the first SoC; and
the first hardware processor executes the first computer-executable instructions to:
receive the fifth audio data from the second SoC; and
send the fifth audio data using the first wireless communication interface.

6. The wearable device of claim 1, further comprising:
the first hardware processor executes the first computer-executable instructions to:
responsive to determination of the second audio data, transition the second SoC from a first mode to a second mode, wherein the second mode consumes more electrical power than the first mode.

7. The wearable device of claim 1, further comprising:
the first hardware processor executes the first computer-executable instructions to:
determine that an elapsed time since the third audio data was determined exceeds a second threshold value; and
transition the second SoC from a first mode to a second mode, wherein the second mode consumes less electrical power than the first mode.

8. The wearable device of claim 1, further comprising:
a housing comprising:
a bottom surface and a top surface;
a sensor window in the bottom surface;
a multicolor light emitting diode (LED) proximate to the sensor window;
a first photodiode proximate to the sensor window;
a green LED proximate to the sensor window; and
a second photodiode proximate to the sensor window.

9. The wearable device of claim 1, further comprising:
one or more sensors comprising:
the heart rate monitor,
an accelerometer,
a gyroscope,
a first temperature sensor, and
a second temperature sensor;
a housing comprising:
a bottom surface and a top surface, wherein the first temperature sensor is located in the housing proximate to the bottom surface and the second temperature sensor is located in the housing proximate to the top surface; and
the second hardware processor executes the second computer-executable instructions to:
determine at least a portion of the sensor data based on output from the one or more sensors; and
send, using the first wireless communication interface, the at least a portion of the sensor data.

10. The wearable device of claim 1, further comprising:
a pressure sensor; and
the first hardware processor executes the first computer-executable instructions to:
determine pressure data using the pressure sensor; and
determine that one or more values of the pressure data are equal to or greater than a second threshold value;
wherein the determining of the sensor data is responsive to the one or more values of the pressure data exceeding the second threshold value.

11. The wearable device of claim 1, further comprising:
one or more sensors comprising:
the heart rate monitor,
an accelerometer,
a gyroscope,
a temperature sensor, and
a pressure sensor;

a housing comprising:

a bottom surface and a top surface, wherein the temperature sensor and the heart rate monitor are located in the housing proximate to the bottom surface; and the second hardware processor executes the second computer-executable instructions to:

determine pressure data from the pressure sensor;

determine the pressure data is indicative of a pressure on at least the bottom surface of the housing that is equal to or greater than a second threshold value; and based at least in part on the pressure being equal to or greater than the second threshold value, operate one or more of the one or more sensors.

12. A device comprising:

at least one microphone;

a first wireless communication interface;

one or more sensors comprising: a heart rate monitor, an accelerometer, a gyroscope, a temperature sensor, and a pressure sensor;

a housing comprising: a bottom surface and a top surface, wherein the temperature sensor and the heart rate monitor are located proximate to the bottom surface;

a first system comprising:

a first memory storing first computer-executable instructions; and a first hardware processor that executes the first computer-executable instructions to:

acquire first audio data using the at least one microphone;

determine second audio data using a first voice activity detector to determine a portion of the first audio data that is representative of speech;

send the second audio data to a second system; and the second system comprising:

a second memory storing second computer-executable instructions; and a second hardware processor that executes the second computer-executable instructions to:

determine pressure data using the pressure sensor;

determine the pressure data is indicative of a pressure that is equal to or greater than a threshold value;

based at least in part on the pressure being equal to or greater than the threshold value, acquire the first audio data;

based at least in part on the pressure being equal to or greater than the threshold value, operate one or more of the one or more sensors;

receive the second audio data; and determine third audio data using a second voice activity detector to determine a portion of the second audio data that is representative of speech.

13. The device of claim 12, wherein:

the first voice activity detector uses a first voice detection algorithm with a first set of one or more threshold values, and the second voice activity detector uses a second voice detection algorithm with a second set of one or more threshold values.

14. The device of claim 12, wherein:

the second hardware processor executes the second computer-executable instructions to:

compress the third audio data to produce fourth audio data;

encrypt the fourth audio data to produce fifth audio data; and store the fifth audio data.

15. The device of claim 12, further comprising:

a load switch that controls power to the second system; wherein:

the first hardware processor executes the first computer-executable instructions to:

responsive to the determination of the second audio data, operate the load switch to provide electrical power to the second system.

16. The device of claim 12, wherein the first hardware processor executes the first computer-executable instructions to:

determine sensor data using the heart rate monitor; and determine that one or more values in the sensor data exceed a second threshold value;

wherein acquisition of the first audio data is responsive to the one or more values in the sensor data exceeding the second threshold value.

17. The device of claim 12, further comprising:

a housing comprising:

a bottom surface and a top surface;

a sensor window in the bottom surface;

a multicolor light emitting diode (LED) proximate to the sensor window;

a first photodiode proximate to the sensor window;

a green LED proximate to the sensor window; and a second photodiode proximate to the sensor window.

18. A device comprising:

at least one microphone;

a first wireless communication interface;

a housing comprising: a bottom surface, a top surface, a sensor window in the bottom surface, a multicolor light emitting diode (LED) proximate to the sensor window, a first photodiode proximate to the sensor window, a green LED proximate to the sensor window, and a second photodiode proximate to the sensor window;

a first system comprising:

a first memory storing first computer-executable instructions; and a first hardware processor that executes the first computer-executable instructions to:

acquire first audio data using the at least one microphone;

determine second audio data using a first voice activity detector to determine a portion of the first audio data that is representative of speech; and send the second audio data to a second system; and the second system comprising:

a second memory storing second computer-executable instructions; and a second hardware processor that executes the second computer-executable instructions to:

receive the second audio data; and determine third audio data using a second voice activity detector to determine a portion of the second audio data that is representative of speech.

19. The device of claim 18, further comprising:

one or more sensors comprising: a heart rate monitor, an accelerometer, a gyroscope, a temperature sensor, or a pressure sensor, wherein the temperature sensor and the heart rate monitor are located proximate to the bottom surface;

wherein the second hardware processor executes the second computer-executable instructions to:

determine pressure data using the pressure sensor;

determine the pressure data is indicative of a pressure that is equal to or greater than a threshold value;

based at least in part on the pressure being equal to or greater than the threshold value, acquire the first audio data; and based at least in part on the pressure being equal to or greater than the threshold value, operate one or more of the one or more sensors.

20. The device of claim 18, further comprising:

a heart rate monitor;

wherein the first hardware processor executes the first computer-executable instructions to:

determine sensor data using the heart rate monitor; and determine that one or more values in the sensor data exceed a threshold value;

wherein the acquisition of the first audio data is responsive to the one or more values in the sensor data exceeding the threshold value.

21. The device of claim 18, further comprising:

one or more sensors comprising: a heart rate monitor, an accelerometer, a gyroscope, a first temperature sensor, and a second temperature sensor, wherein the first temperature sensor is located in the housing proximate to the bottom surface and the second temperature sensor is located in the housing proximate to the top surface; and the second hardware processor executes the second computer-executable instructions to:

determine sensor data based on output from the one or more sensors; and send, using the first wireless communication interface, at least a portion of the sensor data.

* * * * *